United States Patent [19]

Inaoka et al.

[11] Patent Number: 5,521,081
[45] Date of Patent: May 28, 1996

[54] DNA MOLECULE ENCODING PROKARYOTIC PROLYLENDOPEPTIDASE

[75] Inventors: Tetsuya Inaoka, Takatsuki; Toshio Kokubo, Takarazuka; Daisuke Tsuru; Tadashi Yoshimoto, both of Nagasaki, all of Japan

[73] Assignee: Ciba-Geigy (Japan) Limited, Hyogo, Japan

[21] Appl. No.: 227,689

[22] Filed: Apr. 14, 1994

Related U.S. Application Data

[63] Continuation of Ser. No. 917,344, Jul. 23, 1992, abandoned.

[30] Foreign Application Priority Data

Jul. 24, 1991 [EP] European Pat. Off. .............. 91810595
Mar. 12, 1992 [GB] United Kingdom .................. 9205457

[51] Int. Cl.⁶ .............................. C07K 7/08; C12N 9/48; C12N 15/57; C12N 15/63
[52] U.S. Cl. .................. 435/212; 435/240.2; 435/252.3; 435/252.33; 435/254.11; 435/320.1; 530/326; 536/23.2
[58] Field of Search ........................... 536/23.2; 530/300; 435/320.1, 240.2, 252.33, 91.41, 212

[56] References Cited

U.S. PATENT DOCUMENTS 4,865,974   9/1989   Ben-Bassat et al. .................... 435/68.1

OTHER PUBLICATIONS

Gerald et al., Biochim. Biophys. Acta 866:1–14 (1986).
Young et al., Science 222:778–782 (1983).
Diefenthal et al., Appl. Microbiol. Biotechnol. 40:90–97 (1993).
Sambrook et al., *Molecular Cloning, A Laboratory Manual*, 2nd Edition, Cold Spring Harbor Lab. Press, Cold Spring Harbor, NY, 1989, pp. 11–1 to 11–19.
1992 Sigma Chemical Co. Catalog, Sigma Chemical Co., St. Louis, MO, 1992, pp. 395, 855–857, 1756.
Yoshimoto, T. et al.; J. Biol. Chem. 255: 4786–4792 (1980).
Nakamura, S. et al.; Chem. Abstracts 113: 110485w (1990).
Garel, M.–C. et al.; J. Biol. Chem 264: 18966–18972 (1989).
Chevallier, S. et al.: Characterization of a Prolyl Endopeptidase from *Flavobacterium meningosepticum*. J. Biol. Chemistry 267: 8192–8199 (1992).
Diefenthal, T.: *F. meningosepticum* F1PEP1 Gene for Proline–Specific Endopeptidase. EMBL DNA Database, Entry FMF1PEP1, Accession Number X63674, (1992).
DeBoer, H. A. et al.: The Tac Promoter: A Functional Hybrid Derived from the TRP and LAC Promoters. Proc. Natl. Acad. Sci. USA 80:21–25 (1983).
Rennex, D. et al.: cDNA Cloning of Porcine Brain Prolyl Endopeptidase and Identification of the Active—Site Seryl Residue. Biochemistry 30: 2195–2203 (1991).
Yoshimoto, T. et al.: Prolyl Endopeptidase from *Flavobacterium Meningosepticum:* Cloning and Sequencing of the Enzyme Gene. J. Biochem. 110:873–878 (1991).

*Primary Examiner*—Robert A. Wax
*Assistant Examiner*—Eric Grimes
*Attorney, Agent, or Firm*—Wenderoth, Lind & Ponack

[57] ABSTRACT

The invention concerns DNA encoding prolylendopeptidase, hybrid vectors containing such DNA, transformed hosts capable of expressing prolylendopeptidase, a process for the production of prolylendopeptidase including the steps of: culturing a host organism transformed with an expression vector including a DNA coding for prolylendopeptidase and optionally, recovering the produced prolylendopeptidase; and a process for the production of a C-terminal amidated peptide from two precursors, including the steps of: placing the two precursors in contact with a prolylendopeptidase in a medium to convert the precursor peptides to the C-terminal amidated peptide, and recovering the resulting C-terminal amidated peptide.

17 Claims, 4 Drawing Sheets

DNA MOLECULE ENCODING PROKARYOTIC PROLYLENDOPEPTIDASE

This application is a continuation of now abandoned application, Ser. No. 07/917,344, filed Jul. 23, 1992, now abandoned.

The present invention relates to recombinant DNA coding for prolylendopeptidase and a process for the production of said DNA, a host transformed with the recombinant DNA and a process for the production of said transformed host, a process for the production of prolylendopeptidase using the transformed host, and use of the prolylendopeptidase to produce a physiologically active L-terminally amidated peptide.

BACKGROUND OF THE INVENTION

Prolylendopeptidase was first found in human uterus by Walter et al., in 1971 as a specific endopeptidase which cleaves a peptide at the carboxyl- terminus side of a proline residue (Walter, R. et al. Science, 1971, 173, 827–829), and ever since the enzyme has been continuously studied with regard to its physiological role.

On the other hand an endopeptidase showing a very similar specificity to mammalian prolylendopeptidase was found from a bacterium, *Flavobacterium meningosepticum* in 1978 (Yoshimoto, T., et al. Agric. Biol. Chem. 1978,42, 2417–2419). This finding enabled a larger amount to be prepared (but still at a lab scale) of the enzyme, and prolylendopeptidase became available for specific cleavage (Yoshimoto, T., et al. J. Biol. Chem. 1980, 255,4786–4792.) of proteins and peptides. Its unique specificity, recognizing proline residues, makes the enzyme quite useful as a basic tool of protein engineering and draws more attention to the study of the structure and function relationship. The preparation of prolylendopeptidase from *F. meningosepticum*, however, has the following two crucial drawbacks arising from the bacterium. 1) The bacterium is pathogenic (Yoshimoto, T. et al., 1978, supra; Buchanan, R. E. et al. "Bergey's Manual of Determinative Bacteriology," 8th ed. 1974, The Williams & Wilkins Co., Baltimore.) and 2) it produces not only prolylendopeptidase but also significant amounts of other specific or non-specific peptidases (Yoshimoto, T. et al., 1978 supra). These problems have prevented industrial production of the endopeptidase, in spite of a growing demand for the enzyme.

Japanese Unexamined Patent Publication (KOKAI) No. H2-5880 describes cloning of post-proline peptidase gene derived from *Bacteroides gingivalis*, but this enzyme is clearly different from the present enzyme in that the former cleaves glycyl-proline-4-methoxy-β-naphtylamide which cannot be cleaved by the present prolylendopeptidase.

D. Rennex et al., Biochemistry 30,2195–2203, 1991 describe a cloning of cDNA for prolylendopeptidase from the porcine brain, but does not describe an expression of the cDNA.

It is believed that prolylendopeptidase is useful for modification of peptides, for example, C-terminal amidation of biologically active peptides such as LH-RH, oxytocin, calcitonins or the like, but for this purpose, it is necessary to obtain a large amount of the enzyme. Moreover, the enzyme preparation should be free of other peptidases, to ensure a desired reaction. Thus, the production of the enzyme by a gene recombination process is essential.

SUMMARY OF THE INVENTION

Accordingly, the present invention provides a process for the production of prolylendopeptidase by gene engineering.

As a precondition of the recombinant process, the present invention also provides recombinant DNA molecules comprising a gene coding for prolylendopeptidase and a process for the production thereof, as well as a host transformed with the recombinant DNA molecule and a process for the production thereof.

More particularly, the present invention provides a process for the production of a recombinant DNA molecule comprising a gene coding for prolylendopeptidase, comprising the steps of preparing cDNA or genomic DNA from cells, preferentially bacterial cells, capable of producing prolylendopeptidase, inserting DNA fragments coding for prolylendopeptidase into a cloning vector, and selecting a hybrid vector containing the DNA coding for prolylendopeptidase.

The present invention also relates to the DNA molecules prepared as above.

The present invention also relates to an expression vector comprising a gene coding for prolylendopeptidase of any origin and expression control sequences operably linked with the gene.

The present invention further provides a host transformed with the gene coding for prolylendepeptidase of any origin, and capable of producing the prolylendopeptidase.

The present invention still further provides a process for the production of prolylendopeptidase comprising the steps of:

culturing a host organism transformed with an expression vector comprising a DNA coding for prolylendopeptidase to produce the prolylendopeptidase, and optionally, recovering the produced prolylendopepfidase.

The present invention further provides a process for the production of a C-terminal amidated peptide from two precursors thereof, wherein one of the precursors is a precursor peptide forming N-terminal region of the C-terminal amidated peptide and having a proline residue at its C-terminus and another precursor is a precursor peptide or amino acid forming a C-terminal portion of the C-terminal amidated peptide which precursor peptide or amino acid has been C-terminally amidated, comprising the steps of:

placing the two precursors in contact with a prolylendopeptidase in a medium to convert the precursor peptides to the C-terminal amidated peptide, and recovering the resulting C-terminal amidated peptide.

DETAILED DESCRIPTION OF THE INVENTION

Preparation of gene coding for prolylendopeptidase

Hereinafter, the term prolylendopeptidase is intended to include any prolylendopeptidase. The preferred meanings of the term, however, is a prolylendopeptidase derived from prokaryotes, preferably from *Flavobacterium spec*, in particular from *F. meningosepticum*, most preferentially from *F. meningospticum* strain IFO 12535 (ATCC 13253).

Accordingly, a DNA of the present invention coding for a prolylendopeptidase may be cloned from any cell containing a gene coding for prolylendopeptidase, including eucaryotes such as mammals and prokaryotes such as bacteria. In the case a mammalian source, for example the uterus of a mammal, e.g., of human, is chosen, the DNA coding for prolylendopeptidase is preferentially derived from the RNA via cDNA production.

A preferred source for DNA coding for prolylendopeptidase is a bacterium belonging to the genus *Flavobacterium*, in particular *F. meningosepticum*, most preferentially *F. meningosepticum* strain IFO 12535 (ATCC 13253).

Since DNA derived from a prokaryote such as bacterium, for example, *F. meningosepticum*, does not include introns, a genomic DNA can be used to clone a prolylendopeptidase-encoding DNA if a prokaryotic cell is chosen as source. In this case, bacterial cells which produce prolylendopeptidase, for example, cells of *F. meningosepticum*, are homogenised and a whole genomic DNA is extracted according to a conventional procedure (Saito, H. et al. Biochim. Biophys. Acta, 1963, 72, 619–629). The extracted DNA is then digested completely or partially with an appropriate restriction enzyme such as Bgl II, Eco RI, Hinc II, Hind IH, Pst I or Bam HI. The digestion product is then preferably subjected to preparative electrophoresis with low-melting-point agarose gel to enrich DNA fractions of a certain length. This is intended to enrich DNA fragments encoding prolylendopeptidase. Next, the DNA fragments are cloned into a suitable cloning vector. The cloning vector may be derived from any vector useful in the art of genetic engineering, such as from viruses, phages, cosmids, plasmids or chromosomal DNA, for example derivatives of SV40, Herpes-viruses, Papilloma viruses, Retroviruses, Baculovirus, phage λ, e.g., NM989 or EMBL4, or phage M13, bacterial plasmids, e.g. pBR322, pUC18, pSF2124, pBR317 or pPLMu., or yeast plasmids, e.g. yeast 2 μ plasmid, or also chromosomal DNA comprising an origin of replication or an autonomously replicating sequence (ARS). Preferably, the cloning vector is a bacterial vector such as pBR322, pUC18, pUC19 or the like.

Alternatively, a cDNA library may be prepared from a cell expressing prolylendopeptidase, e.g. from a bacterial cell such as preferably from a bacterium belonging to the genus *Flavobacterium*, in particular *F. meningosepticum*, most preferentially *F. meningosepticum* strain IFO 12535 (ATCC 13253), or from a eukaryotic cell or tissue, e.g. mammalian cell or tissue, which produces prolylendopeptidase. For example, RNA is extracted from the human uterus and enriched for mRNA according to a conventional procedure. Next, a cDNA library is constructed according to a conventional procedure such as the Okayama-Berg method (Okayama, H. et at. Mol. Cell. Biol. 1982, 2, 161–170), the method of Gubler and Hoffman (Gubler, U. et al. Gene, 1983, 25,263–270) or the like.

A variety of methods are known in the art for the incorporation of double-stranded cDNA or genomic DNA into an appropriate vector. For example, complementary homopolymer tracts may be added to the double-stranded DNA and the vector DNA by incubation in the presence of the corresponding deoxynucleoside triphosphates and an enzyme such as terminal deoxynucleotidyl transferase. The vector and double-stranded DNA are then joined by base pairing between the complementary homopolymefic tails and finally ligated by specific joining enzymes such as ligases. Other possibilities are the addition of synthetic linkers to the termini of the double-stranded DNA, or the incorporation of the double-stranded DNA into the vector by blunt- or staggerM-end ligation.

Screening of the genomic DNA library or cDNA library is preferably achieved using a DNA hybridization probe. Suitable DNA probes are DNAs of known nucleotide sequence consisting of at least 17 nucleotides, for example synthetic DNAs, cDNAs derived from mRNA coding for prolylendopeptidase, or genomic DNA fragments comprising e.g. adjacent DNA sequences which are isolated from a natural source or from a genetically engineered microorganism.

To design synthetic DNA probes for screening the above-mentioned genomic DNA library or cDNA library, prolylendopeptidase for which a DNA coding region is to be cloned is purified, and its partial amino acid sequence is determined according to a conventional procedure. Next, DNA sequences are designed on the basis of the partial amino acid sequence thus determined. Where an exact nucleotide sequence coding for the amino acid sequence is not known, a combination of nucleotide sequences which partially or totally cover possible nucleotide sequences present due to the degeneracy of genetic codon may be used. Alternatively, the third nucleotide in a codon may be replaced with inosine.

Synthetic DNA probes are synthesized according to known methods, for example by stepwise condensation using the solid phase phosphotriester, phosphite triester or phosphoramidite method, e.g., the condensation of dinucleotide coupling units by the phosphotriester method. These methods are adapted to the synthesis of mixtures of the desired oligonucleotides by using mixtures of two, three or four nucleotides dA, dC, dG and/or dT in protected form or the corresponding dinucleotide coupling units in the appropriate condensation step as described by Y. IKe et al. (Nucleic Acids Research 11, 477,1983).

For hybridization, the DNA probes are labelled, e.g. radioactively labelled by the well known kinase reaction. The hybridization is performed according to known procedures, i.e., in buffer and salt solutions containing adjuncts, e.g. calcium chelators, viscosity regulating compounds, proteins, non-homologous DNA and the like, at temperatures favoring selective hybridization, e.g., between 0° C. and 80° C., for example between 25° C. and 50° C.

In the preferred embodiment, the DNA library of *F. meningosepticum* is used to transform an appropriate host such as *E. coli* cells, which are then plated and cultured on a solid medium to develop colonies, and positive clones are selected by a colony hybridization method using the above-mentioned DNA probes. The transformation of appropriate host cells with the DNA library and the selection and multiplication of transformed host cells are well known in the art. Examples of such methods are given below.

The nucleotide sequence of DNA selected as described above can be determined by methods known per se; for example, by the Maxam-Gilbert method using end-labelled DNA or by the dideoxy chain termination method of Sanger.

A nucleotide sequence of genomic DNA of *Flavobacterium meningosepticum* origin coding for prolylendopeptidase and a corresponding amino acid sequence are shown in the Sequence Listing, SEQ ID No. 1.

Once a nucleotide sequence coding for, or an amino acid sequence of, prolylendopeptidase is determined, a DNA coding for the enzyme also can be prepared by an in vitro synthesis according to conventional methods. Suitable methods of the synthesis of DNA have been presented in summary form by S. A. Narang (Tetrahedron 39, 3, 1983). The known synthesis techniques allow the preparation of polynucleotides up to 120 bases in length, in good yield, high purity and in a relatively short time. Suitably protected nucleotides are linked with one another by the phosphodiester method (K. L. Agarwal et al., Angew. Chemie 84, 489, 1972), the more efficient phosphotriester method (C. B. Reese, Tetrahedron 34, 3143, 1978), the phophite triester method (R. L. Letsinger et al., J. Am. Chem. Soc. 98, 3655, 1976) or phosphoramidite method (S. L. Beaucage and M. H. Carruthers, Tetrahedron Letters 22, 1859,1981).

Simplification of the synthesis of the oligonucleotides and polynucleotides is made possible by the solid phase method, in which the nucleotide chains are bound to a suitable polymer. H. Rink et al. (Nucl. Acids Research 12, 6369, 1984) use trinucleotides instead of individual nucleotides and link them by the phosphotriester method in the solid phase synthesis. A polynucleotide can thus be prepared in a short time and with good yields. The actual double-stranded DNA is built up enzymatically from chemically prepared overlapping oligonucleotides from both DNA strands, which are held together in the correct arrangement by base-pairing and are then chemically linked by the enzyme DNA ligase. Another possibility comprises incubating overlapping single oligonucleotides from the two DNA strands in the presence of the four required deoxynucleoside triphosphates with a DNA polymerase, for example DNA polymerase I, the Klenow fragment of polymerase I or T4DNA polymerase, or with AMV (avian myeloblastosis virus) reverse transcriptase. The two oligonucleotides are thereby held together in the correct arrangement by base-pairing and are supplemented with the required nucleotides by the enzyme to give a complete double-stranded DNA (Scarpulla et at., Anal. Biochem. 121,356, 1982).

Hybrid vector containing gene coding for prolylendopeptidase

In the present invention, hybrid vectors include a hybrid vector for cloning or amplifying a desired prolylendopeptidase gene, and expression vectors. A hybrid vector of the invention comprises a DNA sequence coding for prolylendopeptidase defined hereinbefore.

The hybrid vectors are derived from any vector useful in the art of genetic engineering, such as from viruses, phages, cosmids, plasmids or chromosomal DNA, for example derivatives of SV40, Herpes-viruses, Papilloma viruses, Retroviruses, Baculovirus, phage λ, e.g. NM989 or EMBL4, or phage M13, bacterial plasmids, e.g. pBR322, pUC18, pSF2124, pBR317 or pPLMu., or yeast plasmids, e.g. yeast 2 μ plasmid, or also chromosomal DNA comprising an origin of replication or an autonomously replicating sequence (ARS), or a defective virus, phage or plasmid in the presence of a helper virus, phage or plasmid allowing replication of said defective virus, phage or plasmid, e.g. M13(+)KS vector in presence of e.g. M13K07 helper phage. The Baculoviruses which can be used in the present invention are, for example, *Autographa californica* nuclear polyhedrosis virus (AcMNPV), *Trichoplusia ni* MNPV, *Rachiplusia ou* MNPV, *Galleria mellonella* MNPV, *Bombyx mori* nuclear polyhedrosis virus (BmNPV), and the like. A kit comprising a combination of an *Autographa californica* nuclear polyhedrosis virus and baculovirus transfer vectors pAc700, pAc701, pAc702, pVL1392 and pVL1393 is commercially available from Invitrogen.

A suitable vector of the invention is a vector which is operable in the microbial host cell chosen for multiplying the hybrid vector for the expression of prolylendopeptidase. Suitable vectors contain a complete replicon and a marker gene, which renders possible the selection and identification of the microorganisms transformed by the expression plasmids by means of a phenotype feature.

Thus, the hybrid vectors of the invention provide for replication of a desired prolylendopeptidase DNA in a suitable host, either as an extrachromosomal element or by integration in the host chromosome. Several possible vector systems are available for integration and expression of the cloned DNA of the invention. In principle, all vectors which replicate and/or comprise a recombinant gene which can be expressed in the chosen host are suitable. The vector is selected depending on the host cells envisaged for transformation. In general, such host cells may be prokaryotic or eukaryotic microorganisms such as bacteria, fungi such as yeasts or filamentous fungi, or cells of higher eukaryotic origin such as animal, for example mammalian or insect, cells. Suitable host cells will be discussed in detail hereinbelow. In principle, the hybrid vectors of the invention comprise a DNA encoding prolylendopeptidase, an origin of replication or an autonomously replicating sequence, optionally dominant marker sequences, and, optionally, additional restriction sites.

An origin of replication or an autonomously replicating sequence (a DNA element which confers autonomously replicating capabilities to extrachromosomal elements) is provided either by construction of the vector to include an exogenous origin such as derived from Simian virus (SV40) or another viral source, or by the host cell chromosomal mechanisms.

A hybrid vector of the invention may contain selective markers depending on the host which is to be transformed, selected and cloned. Any marker gene can be used which facilitates the selection of transformants due to the phenotypic expression of the marker. Suitable markers are particularly genes from which a polypeptide can be expressed which provides resistance against compounds toxic to the receipt organism or which completes the enzyme system of a mutant lacking such an essential polypeptide, e.g. of an auxotrophic mutant. Suitable marker genes express, for example, antibiotic resistance, e.g. against tetracycline, ampicillin, or cycloheximide or provide for prototrophy in an auxotrophic mutant, for example in a yeast deficient in the ura3, leu2, his3 or trp1 gene. It is also possible to employ as markers structural genes which axe associated with an autonomously replicating segment providing that the host to be transformed is auxotrophic for the product expressed by the marker.

Within the meaning of hybrid vectors of the invention are also hybrid expression vectors for the expression of prolylendopeptidase. They have in general the same features as the hybrid vectors described hereinbefore, and additionally comprise expression control sequences allowing the production and, optionally, the secretion of prolylendopeptidase. Thus, hybrid expression vectors of the invention comprise a promoter region operably linked with a structural gene encoding prolylendopeptidase and, optionally, a DNA fragment encoding a leader or signal peptide, a transcriptional enhancer, a ribosomal binding site, a transcriptional terminator region and/or further regulatory sequences.

A wide variety of promoter sequences may be employed, depending on the nature of the host cell. Promoters that are strong and at the same time well regulated are the most useful. Sequences for the initiation of translation are for example Shine-Dalgarno sequences. Sequences necessary for the initiation and termination of transcription and for stabilizing the mRNA are commonly available from the noncoding 5'-regions and 3'-regions, respectively, of viral or eukaryotic cDNAs, e.g from the expression host.

Examples of suitable promoters are $\lambda kP_L$, $\lambda P_R$, or $\lambda N$, *E. coli* lac, trp, tac, or lpp, yeast TRP 1-, ADHI-, ADHII-, PHO3-, PHO5-, or glycolytic promoters such as the promoter of the enolase, glyceraldehyde-3-phosphate dehydrogenase, 3-phosphoglycerate kinase (PGK), hexokinase, pyruvate decarboxylase, phosphofructoldnase, glucose-6-phosphate isomerase, 3-phosphoglycerate mutase, pyruvate kinase, triosephosphate isomerase, phosphoglucose isomerase and glucokinase genes, or promoters derived from eukaryotic viruses, e.g. SV40, Rous sarcoma virus, adenovirus 2, bovine papilloma virus, papovavirus, cytomegalovirus or Baculovirus, e.g. *Autographa californica* nuclear polyhedrosis virus (AcMNPV), *Trichoplusia ni* MNPV, *Rachiplusia ou* MNPV, *Galleria mellonella* MNPV, derived promoters or mammalian cell derived promoters, e.g. of the actin, collagen, myosin, or β-globin gene. A preferred eukaryotic promoter is a polyhedrin gene promoter of a Baculovirus, preferentially of the *Autographa californica* nuclear polyhedrosis virus (AcMNPV). The eukaryotic promoters may be combined with enhancing sequences such as the yeast upstream activating sequences (UAS) or viral or cellular enhancers such as the cytomegalovirus IE enhancers, SV40 enhancer, immunoglobulin gene enhancer or others.

Enhancers useful for the expression are transcription-stimulating DNA sequences, e.g. derived from viruses such as Simian virus, Cytomegalovirus, polyoma virus, bovine papilloma virus or Moloney sarcoma virus, or of genomic origin. An enhancer sequence may also be derived from the extrachromosomal ribosomal DNA of *Physarum polycephalum* (PCT WO 86/00089), or it may be the upstream activation site from the acid phosphatase PH05 gene (EP-B-0 213 593), or the PH05, up, PH05-GAPDH hybrid (EP-B-0 213 593), or the like promoter.

Signal sequences which can be used for the present invention may be, for example, a presequence or secretory leader directing the secretion of the polypeptide, or the like. Signal sequences which can be used in the present invention are known in the literature, e.g. compiled in von Heijne, G., Nucleic Acids Res. 14, 4683 (1986). Another suitable signal sequence extends from amino acid 1 to 19 of the amino acid sequence depicted in the sequence listing under SEQ ID No. 1. This signal sequence alone as well as a DNA molecule encoding same, preferably the DNA molecule represented by nucleotides 260 to 316 of SEQ ID No. 1 is also covered by the present invention.

A fibosomal binding site (Shine-Dalgarno Sequence) is either naturally linked to the promoter used or may be located on a short nucleotide sequence which may be covalently linked to the 5' end of the coding region for prolylendopeptidase. Ribosomal binding sites are known in the art.

A promoter chosen for the construction of a hybrid expression vector of the invention may be regulated by a regulatory protein and the production of prolylendopeptidase in the transformed host cell then may be inducible or derepressible. The gene for the regulatory protein may be located either in the genome of the host strain, on an additional plasmid vector the host strain may be cotransformed with, or on the hybrid vector of the invention. The selection of a suitable gene for a regulatory protein depends on the promoter used. The conditions for the induction or depression of the production of prolylendopeptidase also depend on the promoter and on the regulatory protein. A regulatory protein which can be used in the present invention is, for example, a repressor protein, e.g. a product of the trpR, lacI, λcro, or λcI gene, or a temperature sensitive mutant thereof. Preferred hybrid expression vectors of the invention are expression vectors suitable for the expression of mature prolylendopeptidase represented by the amino acid sequence shown in SEQ ID No. 1 in *E. coli*, more preferably such expression vectors comprising a signal sequence, preferably the signal sequence of the prolylendopeptidase gene shown under SEQ ID No. 1, operatively linked with the gene encoding the mature prolylendopeptidase. Most preferred expression vectors are plasmids pFPH5-KD50, pUK-FPEP-a and pUK-FPEP-b characterized in the accompanying examples.

Transformed hosts and preparation thereof

The invention concerns a transformed host cell for multiplicating a recombinant DNA molecules of the invention or particularly for expressing a prolylendopeptidase structural gene comprised in a recombinant DNA molecule of the invention.

The transformed microbial host strains are cultured in a liquid medium containing sources of carbon and nitrogen which can be assimilated by the microbial cell, and inorganic salts, applying methods known in the art. The culture of the hosts is carried out in a conventional nutrient medium which may be supplemented with or deprived of chemical compounds allowing negative or positive selection of the transformants, i.e. such hosts containing the desired DNA molecule together with a selection marker, from the non-transformants, i.e. such hosts lacking the desired DNA molecule.

Any transformable hosts useful in the art may be used, e.g. bacteria, such as *E. coli*, fungi, such as *Saccharomyces cerevisiae*, *Kluyveromyces lactis*, or filamentous fungi, such as *Aspergillus Spec.*, e.g. *A. nidulans*, *A. oryzae*, *A. carbonarius*, *A. awamori* or *A. niger*. However, the use of suitable hosts which are devoid of or poor in restriction enzymes or modification enzymes may be advantageous. Examples of such hosts are bacteria, e.g. *Bacillus subtilis*, *Bacillus stearothermophilus*, *Pseudomonas*, *Haemophilus*, *Streptococcus* and others, and yeasts, for example *Saccharomyces cerevisiae*, and in particular strains of *Escherichia coli*, for example *E. coli* X1776, *E. coli* Y1090, *E. coli* W3110, *E. coli* HB101/LM1035, *E. coli* JA 221, *E. coli* DH5α, or preferentially *E. coli* DH5αF', JM109, MH1 or HB101, or *E. coli* K12 strain. Further suitable hosts are cells of higher organisms, in particular established continuous human or animal cell lines, e.g. human embryonic lung fibroblasts L132, human malignant melanoma Bowes cells, HeLa cells, SV40 virus transformed kidney cells of African green monkey COS-7 or Chinese hamster ovary (CHO) cells. Other suitable host cells are established insect cell lines, for example, *Spodoptera frugiperda*, such as Sf21 or preferentially Sf9 (ATCC CRL 17 11 ), *Mamestra brassicae*, *Bombyx mori* cell systems using *Bombyx mori* nuclear polyhedrosis virus (BmNPV) and the like.

The invention concerns also a method for the preparation of such transformed hosts comprising treatment of a suitable host cell under transforming conditions with a, recombinant DNA molecule of the present invention, especially a hybrid vector of the invention, optionally together with a selection marker gene and optionally selecting the transformants.

Transformation of microorganisms is carried out according to conventional methods as described in the literature, for example for *S. cerevisiae* (A. Hinnen et al., Proc. Natl. Acad Sci. USA, 75, 1929, 1978), for *B. subtilis* (Anagnostopoulos et at., J. Bacteriol. 81,741, 1961), and for *E. coli* (M. Mandel et al., J. Mol. Biol. 53, 159, 1970).

Accordingly, the transformation procedure of *E. coli* cells includes, for example, $Ca^{2+}$ pretreatment of the cells so as to allow DNA uptake, and incubation with the hybrid vector. The subsequent selection of the transformed cells can be achieved, for example, by transferring the cells to a selective growth medium which allows separation of the transformed cells from the parent cells dependent on the nature of the marker sequence of the vector DNA. Preferably, a growth medium is used which does not allow growth of cells which do not contain the vector. The transformation of yeast comprises, for example, steps of enzymatic removal of the yeast cell wall by means of glucosidases, treatment of the obtained spheroplasts with the vector in the presence of polyethylene glycol and $Ca^{2+}$ ions, and regeneration of the cell wall by embedding the spheroplasts into agar. Preferably, the regeneration agar is prepared in a way to allow regeneration and selection of the transformed cells as described above at the same time.

Transformation of cells of higher eukaryotic origin, such as mammalian cell lines, is preferably achieved by transfection. Transfection is carried out by conventional techniques, such as calcium phosphate precipitation, microinjection, protoplast fusion, electroporation, i.e. introduction of DNA by a short electrical pulse which transiently increases the permeability of the cell membrane, or in the presence of helper compounds such as diethylaminoethyl-dextran, dimethyl sulfoxide, glycerol or polyethylene glycol, and the like. After the transfection procedure, transfected cells are identified and selected e.g. by cultivation in a selective medium chosen depending on the nature of the selection marker, for example standard culture media such as Dulbecco's modified Eagle medium (DMEM), minimum essential medium, RPMI 1640 medium and the like, containing e.g. the corresponding antibiotic.

The transformed host cells are cultured by methods, known in the art in a liquid medium containing assimilable sources of carbon, e.g. carbohydrates such as glucose or lactose, nitrogen, e.g. amino acids, peptides, proteins or their degradation products such as peptones, ammonium salts or the like, and inorganic salts, e.g. sulfates, phosphates and/dr carbonates of sodium, potassium, magnesium and calcium. The medium furthermore contains, for example, growth-promoting substances, such as trace elements, for example iron, zinc, manganese and the like.

The medium is preferably so chosen as to exert a selection pressure and prevent the growth of cells which have not been transformed or have lost the hybrid vector. Thus, for example, an antibiotic is added to the medium if the hybrid vector contains an antibiotic resistance gene as marker. If, for instance, a host cell is used which is auxotrophic in an essential amino acid whereas the hybrid vector contains a gene coding for an enzyme which complements the host defect, a minimal medium deficient of the said amino acid is used to culture the transformed cells.

Cells of higher eukaryotic origin such as mammalian cells are grown under tissue culture conditions using commercially available media, for example Dulbecco's modified Eagle medium (DMEM), minimum essential medium, RPMI 1640 medium and the like as mentioned above, optionally supplemented with growth-promoting substances and/or mammalian sera. Techniques for cell cultivation under tissue culture condition are well known in the art and include homogeneous suspension culture, e.g. in an airlift reactor or in a continuous stirrer reactor, or immobilized or entrapped cell culture, e.g. in hollow fibers, microcapsules, on agarose microbeads, porous glass beads, ceramic cartridges, or other microcarriers.

Culturing is effected by processes which are known in the art. The culture conditions, such as temperature, pH value of the medium and fermentation time, are chosen so that a maximum expression level of the polypeptide or derivative of the invention is obtained. Thus, an *E. coli* or yeast strain is preferably cultured under aerobic conditions by submerged culture with shaking or stirring at a temperature of about 20° C. to 40° C., preferably at about 30° C., and a pH value of 4 to 8, preferably of about 7, for about 4 to 30 hours, preferably until maximum yields of the polypeptide or derivative of the invention are reached.

Production of prolyendopeptidase

The present invention concerns also a method for the production of prolylendopeptidase.

For the expression of prolylendopeptidase, either procaryotic or eucaryotic host cells may be used, e.g. *E. coli* strains defective in protease genes, e.g. in the 1 on protease gene, and genes involved in the regulation of heat shock induced protein synthesis, e.g. in the htpR gene (U.S. Pat. No. 4,758,512; Buell, G. et at., Nucleic Acids Res. 13: 1923–1938, 1985).

Preferably, prolylendopeptidase is produced using *E. coli*. In this case to improve the expression, a 5'-terminal noncoding region of the cloned DNA is preferably removed while maintaining the full length of the coding region, particularly the coding region of the mature polypeptide shown under SEQ ID No. 1. The coding region is most preferably functionally linked with a signal sequence allowing the secretion of the prolylendopeptidase. Moreover, the structural gene is functionally linked with a promoter region functional in *E. coli*, either heterologous to or natively linked with the prolylendopeptidase coding region. The linkage is performed according to a conventional procedure, for example, using an appropriate restriction enzyme site or deletion by digesting with an exonuclease such as *E. coli* exonuclease III and successive blunting with a nuclease, e.g. mung-bean nuclease.

In one of the most preferable embodiments, a genomic DNA having a linker sequence immediately upstream of a full length coding region for prolylendopeptidase is linked with a heterologous promoter such as tac promoter in an expression vector, for example, a plasmid based on pUC119 plasmid. Very particularly, a coding region in the genomic DNA from *Flavobacterium meningosepticum* encodes a pro-form of prolylendopeptidase, e.g. such consisting of a mature form of the enzyme, for example consisting of amino acid residue 1 to the end of the sequence shown under SEQ ID No. 1, and a signal peptide, for example amino acid residues −19 to −1 of the sequence shown under SEQ ID No. 1. When such a type of an expression plasmid is used to transform *E. coli* host, and the transformant is cultured, then prolylendopeptidase is produced in *E. coli* cells and secreted into the periplasmic region. In the process of secretion the signal peptide is removed to give a mature form of the enzyme which is not incorporated in inclusion bodies, and therefore, the produced prolylendopeptidase is easily recovered.

According to another embodiment of the present invention, a DNA coding for the present enzyme is inserted into a baculovirus transfer vector to construct a recombinant baculovirus transfer vector, and the recombinant baculovirus transfer vector is then co-transfected with a baculovirus DNA to insect cells to carry out a homologous. recombination.

The baculovirus transfer vector is usually a plasmid containing a segment of baculovirus DNA, which segment comprises a gene not essential for the replication of baculovirus. The gene not essential for the replication of baculovirus is, for example, a polyhedrin gene comprising a polyhedrin structure gene and a promoter thereof. Such baculovirus transfer vectors are, for example, pAcYM1 (Matsuura, Y., et al., J. Gen. Virol. (1987) 68, 1233–1250), pAc311, pAc360, pac373, pAc380CUSP4,745,051), pAc700, pAc701, pAc702, pVL1392, pVL1393, and the like. Preferred is the use of pVL1392.

The baculoviruses used in the present invention are, for example, *Trichoplusia ni* MNPV, *Rachiplusia ou* MNPV, *Galleria mellonella* MNPV, and the like. Preferentially used is *Autogapha califonica* nuclear polyhedrosis virus (AcM-NPV). A kit comprising a combination of an *Autographa californica* nuclear polyhedrosis virus and baculovirus transfer vectors pAc700, pAc701, pAc702, pVL1392 and pVL1393 is commercially available from Invitrogen Corp., San Diego, Cailf., USA. The insect cells used in the present invention are established insect cell lines, for example, *Spodoptera frugiperda*, such as Sf21 or preferentially Sf9 (ATCC CRL1711), but also *Mamestra brassicae* and the like. A *Bombyx mori* cell system using *Bombyx mori* nuclear polyhedrosis virus (BmNPV) can also be used in the present invention.

The homologous recombination is carried out in accordance with a conventional procedure as described, for example, in "A Manual of Methods for Baculovirus Vectors and Insect Cell Culture Procedures, M. D. Summers et al., Texas Agricultural Experiment Station Bulletin No. 1555". The transfected insect cells are cultured in accordance with a conventional procedure. Namely, the transfected insect cells may be cultured in any tissue culture medium in which insect cells can grow, such as Grace's or TC100 medium supplemented with mammalian serum, serum-free medium EX-CELL400, or the like, at a temperature of 20° C. to 30° C., preferably 27° C. to 28° C., for example 27° C., for 2 to 10 days, preferably 3 to 5 days.

The expressed prolylendopeptidase can be extracted from microbial cells such as $E.\ coli$ cells or a supernalant of a cell culture by conventional methods, e.g., comprising homogenization of the cells, chromatography such as ion-exchange, hydrophobic or size-exclusion chromatography, precipitation, e.g., with ammonium sulfate or acid, preparative electrophoresis such as polyacrylamide gel electrophoresis or isoelectric focusing, and the like. Particularly, prolylendopeptidase from $Flavobacterium\ meningosepticum$, which is expressed in $E.\ coli$, is easily and selectively extracted from the cells with an osmotic shock method if the enzyme is secreted to the periplasmic region. The obtained crude enzyme can be further purified with usual methods, e.g. comprising chromatography such as ion-exchange, hydrophobic or size-exclusion chromatography, preparative electrophoresis such as polyacrylamide gel electrophoresis, or isoelectric focusing, and the like.

Production of C-terminally amidated peptides

The present invention concerns also a method for the production of C-terminus amidated peptides by use of prolylendopeptidase. Prolylendopeptidase catalyzes not only the hydrolyric cleavage of a peptide at the C-terminus side of a proline residue, but also, forming the peptide bond in the reverse manner of the hydrolysis, the coupling of a peptide fragment to C-terminus of the other fragment which is terminated by a proline residue. Under controlled conditions the coupling reaction is predominant and prolylendopeptidase is used to catalyze coupling of two peptide fragments (or of amino acid to a peptide fragment). The preferable conditions of the coupling are an excess of one of peptide fragments (or an amino acid), and the presence of an organic solvent, such as glycerol, ethylene glycol, butanediol, ethanol, n-propanol, i-propanol, acetonitrile, DMF, and DMSO, in a high concentration, typically more than 50%.

In preferable embodiments of the present invention, biologically active peptides whose C-termini are α-amidated and have proline residues, preferably, at or near their C-termini are prepared with prolylendopeptidase from two precursors thereof, wherein one of the precursors is a precursor peptide forming N-terminal region of the amidated bioactive peptide and having a proline residue at its C-terminus and another precursor is a precursor peptide or amino acid forming a C-terminal portion of the amidated bioactive peptide which precursor peptide or amino acid has been amidated at C-terminus. The α-amidated bioactive peptides prepared with prolylendopeptidase involve aspartocin, bermorphin, calcitonin, CGRP, CGRP II, crustacean erythrophore concentrating hormone, cockroach myoactive peptide I, color change hormone, glumitocin, granuliberin-R, isotocin, LH-RH, mesotocin, morphine modulating neuropeptide, α-MSH, oxytocin, phenypressin, $SCP_A$, $SCP_B$, valitocin, vasopressin, and vasotocin.

The present invention provides a process for the production of a recombinant DNA molecule comprising a gene coding for prolylendopeptidase, comprising the steps of preparing cDNA or genomic DNA from cells, preferentially bacterial cells, capable of producing prolylendopeptidase, inserting DNA fragments coding for prolylendopeptidase into a cloning vector, and selecting a hybrid vector containing the DNA coding for prolylendopeptidase.

The present invention concerns in particular the embodiments disclosed in the examples.

EXAMPLES

Figure 1:
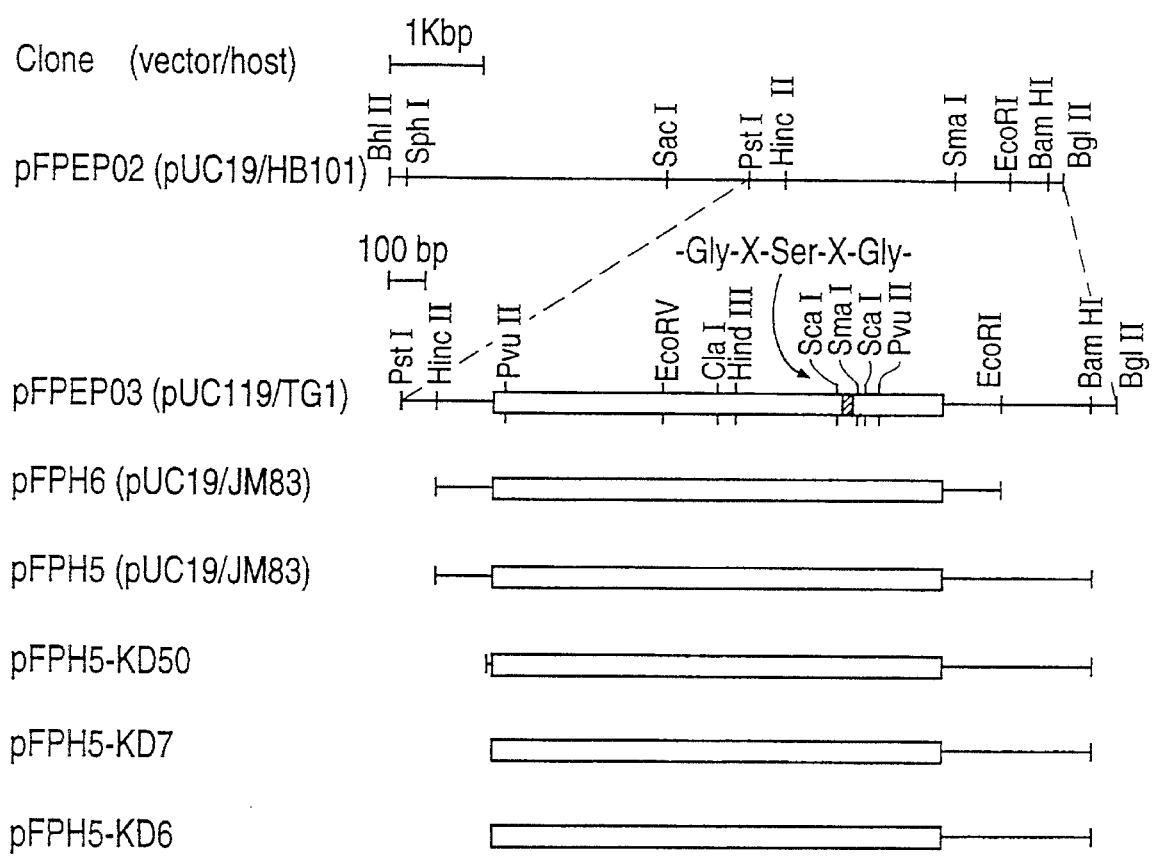
FIG. 1 represents restriction maps of the cloned inserts in pFPEPO2 and pFPEPO3. The open box represents the open reading frame of the prolylendopeptidase gene and the solid box a consensus sequence of the catalytic site of serine protease. Cloned inserts of pFPH6, pFPH5 and its deletion subclones (KD50, KD7 and KD6) are also aligned with the maps on the same scale.

The present invention will now be further illustrated by, but is no means limited to, the following examples.

In the Examples, the following materials and methods are commonly used.

The bacterial strains and plasmids used are listed in Table I.

TABLE 1

Strains and plasmids.

| Strains or plasmids | Relevant genotype |
|---|---|
| Strains | |
| E. Coli | |
| JM 83 | ara, Δ(lac-proAB), rpsL (=straA), Ø80$^r$, lacZ ΔM15 |
| JM 109 | recA1, endA1, gyrA96, thi, hsdR17, supE44, relA1, λ$^-$, Δ(lac-proAB), F'[proAb$^+$, lacI$^q$, lacZ ΔM15, traD36] |
| HB 101 | F$^-$, hsdS20(4$^-$$_B$, m$^-$$_B$), recA13, ara-14, proA2, lacY1, galK2, rpsL20 (Sm$^r$), xyl-5, mtl-1, supuE44, λ$^-$, mcrA$^+$, mcrB$^-$ |
| TG1 | supE, hsd Δ5, thi, D(lac-proAB), F'[proAB$^+$, lacI$^q$, lacZ ΔM15, traD36] |
| F. meningosepticum | IFO 12535 (ATCC 13253) |
| Plasmids | |
| pUC19 | Amp$^r$, lacI', lacZ' |
| pUC118 | Amp$^r$, lacI', lacZ', M13IG |
| pUC119 | Amp$^4$, lacI', lacZ', M13IG |

Transformation, restriction mapping, preparation of plasmids, and other molecular cloning procedures are done by standard methods. (Sambrook, J. et al. "Molecular cloning:

a laboratory manual," 2nd ed. 1989, Cold Spring Harbor Laboratory, Cold Spring Harbor; Silhavy, T. J. et al. "Experiments with gene fusions," 1984, Cold Spring Harbor Laboratory, Cold Spring Harbor.) Restriction enzymes and DNA-modifying enzymes are used according to the recommendations of the manufacturers. Deletion with exonuclease III is carried out by use of a KILO-SEQUENCE DELETION KIT Cyanisch-Perron, C. et al. Gene, 1985, 33, 103–119; Henikoff, S. Gene, 1984, 28, 351–359.). The nucleotide sequences are determined by the dideoxy method, by using a Sequenase kit Genomic DNA from *F. meningosepticum* is isolated by the method of Saito and Miura (Saito, H. et al. Biochim. Biophys. Acta, 1963, 72, 619–629).

Restriction enzymes, DNA-modifying enzymes, the KILO-SEQUENCE DELETION KIT and the MEGALABEL kit axe purchased from Takara Shuzo Co. Ltd. (Kyoto). The SEQUENASE VER.2.0 KIT is the product of U.S. Biochemical Corp. (Cleveland, Ohio). Prolylendopeptidase from *F. meningosepticum* and ENDOPROTEINASE ASP-N are purchased from Seikagaku Corp. (Tokyo) and Boehringer Mannheim- Yamanouchi Co. Ltd. (Tokyo), respectively. The enzyme substrates, Z-Gly-Pro-β-naphthylamide and Z-Gly-Pro- P-nitroanilide, are obtained from Novabiochem AG(Laeufelfingen, Switzerland). Radio isotopes are purchased from Amersham Japan Co. Ltd. (Tokyo) and other biochemicals are obtained from Sigma Chemical Co. (St. Louis, Mo.), Wako Pure Chemical Industries Ltd. (Osaka) and Nacalai Tesque Inc. (Kyoto).

EXAMPLE 1

Preparation of DNA probes

Commercially obtained prolylendopeptidase is purified by reverse phase HPLC on a 4.6×35 mm TSKGEL OCTADECYL NPR COLUMN (Tosoh Co. Ltd.). The column is eluted with 0.01% TFA in water and a 3:1 mixture of $CH_3CN$ and i-PrOH, at a flow rate of 1 ml/min. The gradient from 35–70% of the organic solvent mixture is applied over 40 min. and the major peak is collected.

Since N-terminus of the endopeptidase is blocked, the enzyme must be subjected to proteolytic cleavage to determine its partial primary structure. The proteases commonly used for the cleavage like trypsin do not give satisfactory results. Therefore, proteases and conditions of the hydrolyric cleavage are systematically investigated and ENDOPROTEINASE ASP-N is found to give the best result.

The purified enzyme (0.5 mg) in 10 mM ammonium carbonate, pH 7.9, containing 4mM urea is hydrolyzed by 1 μg of ENDOPROTEINASE ASP-N at 37° C. for 24 h. The peptide mixture obtained by this digestion is separated by reverse phase HPLC on a 4.6×250 mm VYDAC C18 COLUMN (Separations Group Corp.) with the mobile phase of 0.01% TFA in water and a. 3:1 mixture of $CH_3CN$ and i-PrOH. The flow rate is 1 ml/min. The isolated peptides are further purified by rechromatography. The amino acid sequence of the purified fragments are determined by manual Edman degradation using the methods described by Kobayashi and Tarr (Kobayashi, R. et al. Tanpakushitsu Kakusan Koso, 1986, 31,991–1002; Tarr, G. E. "Methods in protein sequencing analysis" (ed. Elzinga, M.), 1982, 223–232, Humana Press, New Jersey).

The nucleotide sequences for the probes are not uniquely determined from the amino acid sequences because of multiple codon usage. Out of the 23 partial amino acid sequences six which give relatively less combinations of possible nucleotide sequences are chosen to make DNA probes ffable II). Preferred codon usage in *F. meningosepticum* has not been known, and two guidefines are adopted in the design of the nucleotide probes. Namely, three of the 6 probes (A-12, 13 and 19) are designed so as to consist of a single oligonucleotide sequence, selecting the most probable codon for each amino acid residue on the assumption that the genome DNA of *F. meningosepticum* is GC rich. The other three (A-3, 9 and 18) are mixtures of oligonucleotides of the possible sequences. To reduce further the number of the possible sequences in the mixture, inosine (I) is placed at the position which can be one of four bases, A, G, C and T, since inosine forms stable base pairs with all of four.

TABLE II

Determined partial amino acid sequences of the fragments of prolylendopeptidase obtained by the ENDOPROTEINASE ASP-N digestion (shown by the amino acid residue No. in SEQ ID No. 1), and corresponding nucleotide positions in SEQ ID No. 1 of the probes designed from the amino acid sequences.

| Fragment No. | Amino acid residue No. in SEQ ID No. 1 | Probe No. | Corresponding nucleotide position in SEQ ID No. 1 |
|---|---|---|---|
| 3 | 499–509 | A-3 | 1811–1833 |
| 9 | 352–364 | A-9 | 1370–1407 |
| 12 | 28–34 | A-12 | 398–414 |
| 13 | 182–190 | A-13 | 860–877 |
| 18 | 380–391 | A-18 | 1454–1485 |
| 19 | 268–276 | A-19 | 1118–1137 |

Oligonucleotides are synthesized with an Applied Biosystems Model 381A DNA synthesizer. After removal of dimethoxytrityl group at the end of the synthetic sequence the oligonucleotides are deprotected and cleaved from the supports, according to the protocols of the manufacturer. The synthesized DNA are then subjected to preparative electrophoresis with 8% polyacrylamide gel in 7M urea. Purified oligonucleotides are extracted from the separated bands and deionized by use of Waters SEP-PACK C-18 COLUMNS.

EXAMPLE 2

Evaluation of the probes

The chromosomal DNA is isolated from *F. meningosepticum* and digested by 4 kinds of commonly used restriction enzymes recognizing hexanucleotide sequence, i.e., PstI, HindIII, EcoRI and BglII.

Oligonucleotide probes are radio-labeled by use of a MEGALABEL kit with $[\gamma-^{32}P]ATP$ to give a specific activity of ca. $1\times10^6$ cpm/pmol. The chromosomal fragments are electrophoresed on a 0.7% agarose gel and transferred to a Millipore nitrocellulose filter by the method described by Sambrook et al. (Sambrook et al., 1989, supra).

After prehybridization according to a standard protocol (Sambrook et al., 1989, supra), hybridization is carried out in 6×SSC hybridization solution with 0.2 pmol/ml of the labeled probe at 45° C. for 16 h. The filter is washed with 6x SSC three times for 3 min. at room temperature and then once for 1 min. at 45° C. Autoradiography is performed with a FUJI BIO-IMAGE ANALYZER BAS 2000. Only the A-3 probe is found to give a clear and specific signal with each of the digested DNA.

EXAMPLE 3

Preparation of genomic library and screening thereof

The molecular weight of prolylendopeptidase is found quite large, 76,000 by SDS-polyacrylamide gel electrophoresis (Yoshimoto et at., 1980, supra). The size of the enzyme corresponds to 2 kb of the coding region in the genome. The larger the cloned DNA fragment is, the higher the chance of including the full length of the open reading frame. Therefore, rather a long fragment but small enough to get a high efficiency in the transformation is desired and 7 kb of the BglII fragment is selected. Namely, genomic DNA digested by BglII is subjected to preparative electrophoresis with low-melting-point agarose and the fraction of the gel containing 7 kb fragments is cut out. The excised gel piece is dissolved in a ligation mixture and the extracted chromosomal fragments are cloned into BamHI site of pUC19. By this ligation mixture *E. coli* HB101 is transformed to give a genomic library comprising about 4,000 recombinants.

The genomic library is screened with the A-3 probe by colony hybridization and 119 positive clones are obtained. Sixteen positive clones are chosen and analyzed further by restriction endonuclease digestion and the enzyme assay. One clone with 7 kb insert is found to show a comparatively high prolylendopeptidase activity. The plasmid is named pFPEP02 and further characterized.

EXAMPLE 4

Restriction mapping and DNA sequencing of the isolated clones

The restriction map of the insert of pFPEP02 is shown in FIG. 1. To locate the coding region the insert DNA is cleaved by appropriate restriction enzymes and subcloned into pUC118 or pUC119. The clone which has 2.6 kb of HincII-EcoRI fragment (pFPH6) shows the highest enzyme activity. To determine the entire nucleotide sequence of this fragment a series of deletion subclones are generated from either end of a larger fragment which includes the 2.6 kb fragment (pFPEP03, deposited as FERM BP-3466). From the deletion mutants and the subcloned restriction fragments, the whole sequence of the 2.6 kb fragment is determined by the dideoxy method (SEQ ID No. 1 ).

The prolylendopeptidase gene is represented by the open box in FIG. 1. The gene is found to have an open reading frame of 2,118 bp, which is preceded by a putative promoter sequence separated by 28 bp from the ATG initiation codon. The endopeptidase, predicted from the nucleotide sequence, consists of 705 amino acid residues with a calculated molecular weight of 78,700, in good agreement with the value of 77,500 determined by sedimentation equilibrium (Yoshimoto, T. et at. Agric. Biol. Chem. 1982, 46, 2157–2158). The enzyme has been thought a serine protease based on the inhibitor study (Yoshimoto et at., 1980, supra). In agreement with the assumption there is a consensus sequence of catalytic site of serine protease, Gly-X-Ser-X-Gly, in the c-terminal region. The G-C content of the cloned HincII-EcoRI fragment is 38.4% and rather low, contrary to expectations. In the protein data banks, NBRF-PIR and SWISS-PROT, no protein which has a significant homology with prolylendopeptidase is found.

EXAMPLE 5

Expression of prolylendopeptidase

For the expression of prolylendopeptidase, *E. coli* transformed with a plasmid is cultured in TY medium at 37° C. with agitation in a rotary shaker (120 rpm). TY-broth used for expression of prolylendopeptidase in *E. coli* contains 1% BACTO-TRYPTONE, 0.1% BACTO-YEAST EXTRACT, 0.1% glucose, 0.8% NaCl, pH 7. *F. meningosepticum* is grown in a polypeptone medium which contains 1% polypeptone, 0.2% BACTO-YEAST EXTRACT, 0.1% $MgSO_{4.7}H_2O$ and 2.5% NaCl (pH7), according to instructions of a culture collection.

Two assay methods (A and B) are employed for qualitative estimation of the enzyme activity and for the quantitative evaluation, respectively. In the method A, Z-Gly-Pro-β-naphthylamide (Z=N-benzyloxycarbonyl) is used as a substrate. To 0.8 ml of 20 mM Tris-HCl buffer, pH 7.0, is added 0.1 ml of *E. coli* culture or diluted cell suspension and the mixture was preincubated at 37° C. for 3 min. The reaction is started by the addition of 0.1 ml of the substrate solution (5 mM) in 40% dioxane and terminated after 10 min. by the addition of 0.5 ml FAST GARNET GBC (4'-amino-2,3'-dimethylazobenzene) solution ( 1 mg/ml) containing 10% Triton X-100 in 1M acetate buffer, pH 4.0. The reaction mixture is left at room temperature for 20 min. and centrifuged at 12,000 g for 5 min. The absorbance of the supernatant is measured at 550 nm.

In the quantitative assay (B), *E. coli* cells are harvested by centrifugation, washed with 0.1M HEPES (pH 7.4), and suspended in the same volume of the HEPES solution as the culture. The cell suspension is sonicated on ice for 60 s with intervals over 3 min. to give a cell lysate. To 0.94 ml of 0.1m potassium phosphate buffer, pH 7.0, is added 0.05 ml of 4 mM Z-Gly-Pro-p-nitroanilide in 40% dioxane. After 3 min. preincubation at 30° C., 0.01 ml of the diluted lysate is added to the mixture and the change of the absorbance is followed at 410 nm with a Hitachi spectrophotometer U-3210 at 30° C. One unit of the enzyme activity is defined as the amount of the enzyme that releases 1 μmol of p-nitroaniline per minute, corresponding to 8.87 OD/min. with this standard procedure.

Although the clone having the HincII-EcoRI fragment (pFPH6) clearly shows the activity of prolylendopeptidase, the activity is much smaller than that of the original bacterium. To improve the expression level, another set of deletion mutants are prepared from the clone having HincII-BamHI fragment (pFPH5). As the deletion is extended from the 5' end of the fragment, the enzyme activity increases gradually to reach maximum with pFPH5-KD50 (FIG. 1 ). And then the activity decreases but still moderate (pFPFH5-KD7), when the deletion reaches to the initial pan of the reading frame. Very little activity is detected from a clone with further deletion (pFPH5-KD6). Therefore, the expression of the enzyme in KD50 is further investigated in detail.

The plasmid pFPH5-KD50 contains 120 bp of upstream noncoding region comprising the putative promoter sequence, together with the full length of the open reading frame. *E. coli* (JM83) transformed by this plasmid is grown in TY medium, and the time-course of the expression of prolylendopeptidase is followed with the enzyme activity of the total protein in homogenate of the washed cell (Table HI). Around 6 to 12 h, as the growth of the bacterium stops, total activity of the enzyme increases rapidly and reaches the maximum value of 3,371 units/L, corresponding to 10 times of the enzyme activity attained by *F. meningosepticum* (346 units/L). The total activity stays constant until 24 h and then slowly decreases. On the other hand, the specific activity shows the rapid increase around 6 to 12 h similar to the total activity, but it increases gradually even after 24 h. A maximal specific activity of 10.6 units/mg protein is reached around 36 h. Since typical specific activity of purified prolylendopeptidase is about 115 units/mg protein, the expression level of prolylendopeptidase in this clone amounts to about 1/10 of the total protein.

Such a high expression level of prolylendopeptidase is also demonstrated in the SDS-PAGE analysis. Sample for SDS-PAGE is prepared by mixing the lysates described before with an equal volume of sample buffer containing SDS and β-mercaptoethanol and incubated at 96° C. for 5 min. The electrophoresis is performed using a precast plate (12.5%, 84×90×1.0 mm) and the apparatus obtained from Daiichi Pure Chemicals Co. Ltd. (Tokyo), according to the protocols given by the manufacturer. The gel is stained with COOMASSIE BRILLIANT BLUE R250 (Acid Blue 83).

At 12 h appearance of a new band is clearly distinguished at the same position as the standard of prolylendopeptidase from *F. meningosepticum*. Intensity of this band is highest around 12–24 h, concomitantly with the change of the total activity of the enzyme.

The production of prolylendopeptidase is shown in the following Table III.

TABLE III

Expression of prolylendopeptidase in *E. coli* (JM83) harboring pFPH5-KD50.

| Time (h) | Absorbance at 550 nm in culture medium | Total activity (unit/L) | Specific activity (unit/mg protein) |
|---|---|---|---|
| 0 | 0.12 | 0 | 0 |
| 6 | 4.14 | 572 | 2.2 |
| 12 | 6.06 | 3371 | 8.8 |
| 24 | 5.75 | 3388 | 9.7 |
| 36 | 5.20 | 3003 | 10.6 |
| 48 | 4.69 | 2494 | 10.5 |

EXAMPLE 6

Further improvement of expression

The expression in *E. coli* JM 83 harboring pFPH5-KD50 has reached quite a high level, but an even higher level would be preferable for the industrial production of prolylendopeptidase. In pFPH5-KD50 a putative promoter sequence, originating from *F. meningosepticum*, is found and assumed to function in *E. coli*. To improve the expression level further, this native promoter is replaced by the strong trp-lac hybrid promoter (or tac promoter), as follows.

Figure 2:
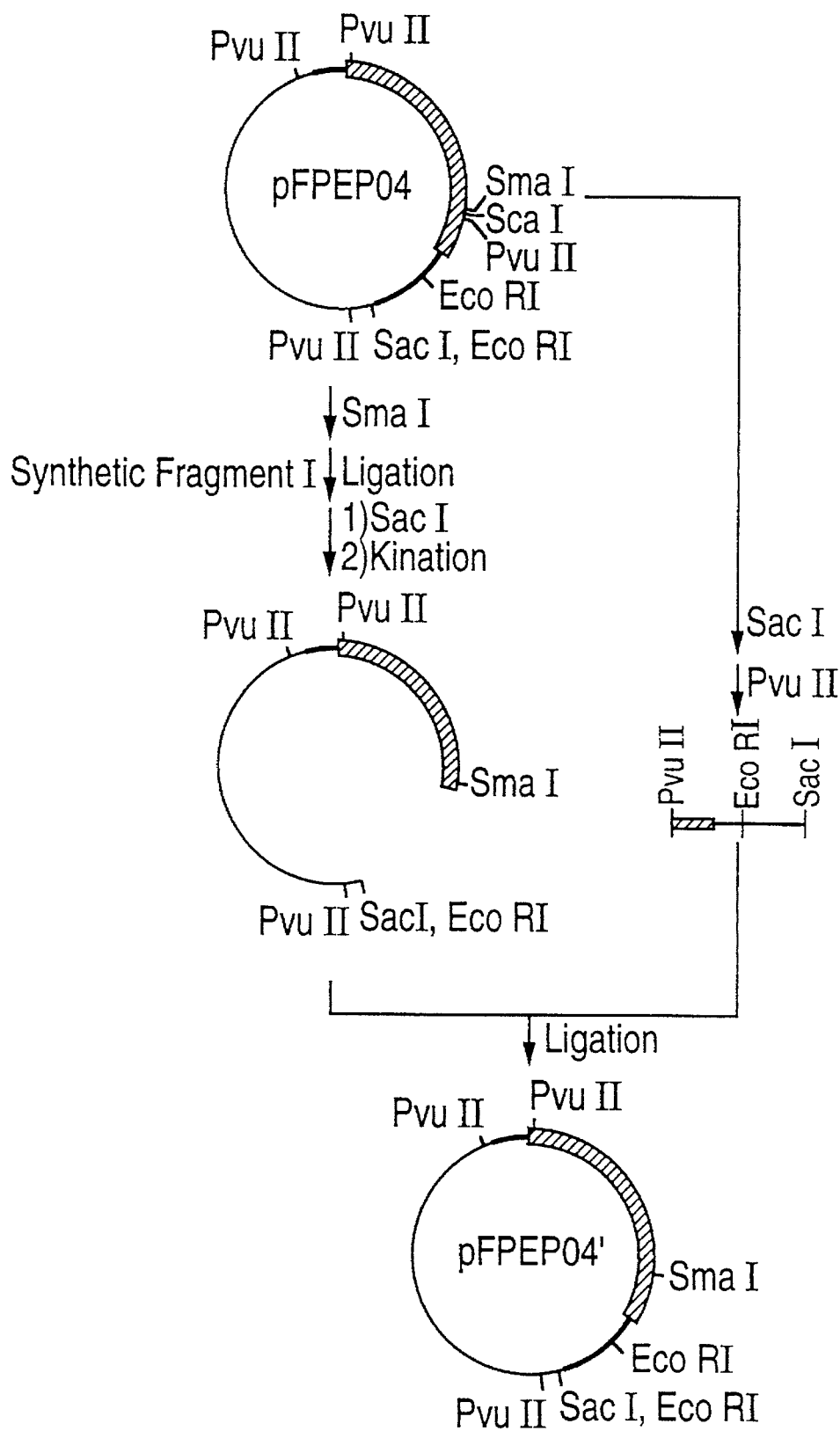
FIG. 2 represents part of the process for construction of expression plasmids pUK-FPEP-a and pUK-FPEP-b starting from an intermediate plasmid pFPEPO4: Construction of pFPEPO4' starting with pFPEPO4.

Plasmid pFPEPO2 is digested with HincII to obtain a 3.1 k bp HincII fragment containing prolylendopeptidase gene, which is then subcloned at the SmaI site of pUC118 by blunt end ligation to give pFPEPO4. After the ligation, the insertion points at the both ends of the fragment are cleavable neither by HincII nor SmaI (FIG. 2). To delete the ScaI and PvuII sites in the coding region the synthetic double-stranded oligonucleotide fragment which corresponds to the sequence between the SmaI and PvuII sites but is mutated at two positions (Synthetic Fragment I, see SEQ ID No. 2) is prepared by annealing the lower strand and the upper strand only whose 5' end has been phosphorylated beforehand by T4 polynucleotide kinase.

On the other hand, the plasmid pFPEPO4 is cleaved at the single SmaI site existing in the open reading frame, and the mutated SmaI-PvuII fragment mentioned above is ligated to the linearized plasmid at both terminus Sinai sites. The ligation product is then digested by SacI and the longer fragment, containing the 5' portion of the coding region, is isolated by agarose gel electrophoresis. After kinasing the isolated fragment the missing piece between PvuII and SacI sites, prepared separately from pFPEPO4, is ligated to construct plasmid pFPEPO4'. Since one nucleotide at the terminus generated by PvuII has been changed in the synthetic fragment, the PvuII site is not regenerated by this cyclization.

Figure 3:
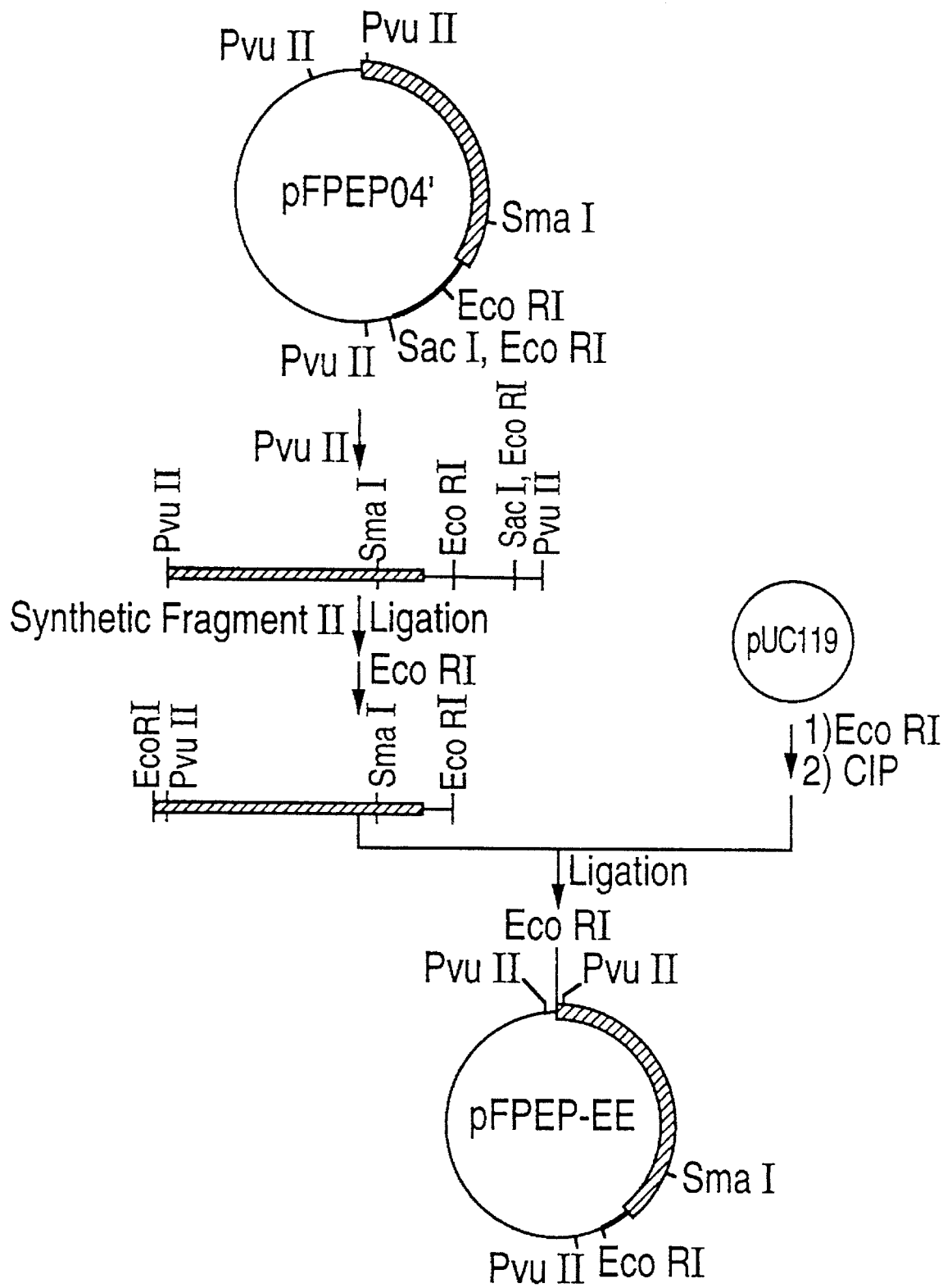
FIG. 3 represents part of the process for construction of expression plasmids pUK-FPEP-a and pUK-FPEP-b starting from an intermediate plasmid pFPEEM: Construction of pFPEP-EE starting with pFPEPO4'.

Next, a new EcoRI site is created immediately upstream from the initiation codon of the prolylendopeptidase gene as follow (see FIG. 3). Synthetic Fragment II (SEQ ID No.3) is prepared by ligation of the four oligonucleotides U 1, U2, L 1 and L2 (see SEQ ID No.4, 5, 6 and 7, respectively), where two of them (U2 and L 1 ) have been phosphorylated at their 5' termini. The prepared fragment corresponds from the initiation codon to PvuII site in the upstream coding region and has protruding cohesive 5' terminus immediately upstream of the initiation site to introduce EcoRI site after ligation. For the following ligation the both 5' ends of the prepared fragment are phosphorylated by T4 polynucleotide kinase.

The plasmid pFPEPO4', in which one of four PvuII has been deleted, is digested with PvuII, and the fragment containing most of the coding region is isolated by agarose gel electrophoresis and ligated to the second synthetic fragment described above. The product obtained by the ligation is digested with EcoRI to isolate the complete open reading frame with the 5' protruding cohesive ends at both termini, which is then subcloned at the EcoRI site of pUC119. The two synthetic regions in the obtained plasmid, pFPEP-EE, are sequenced and the mutated nucleotide sequences are confumed. The resulting plasmid is pFPEP-EE.

Figure 4:
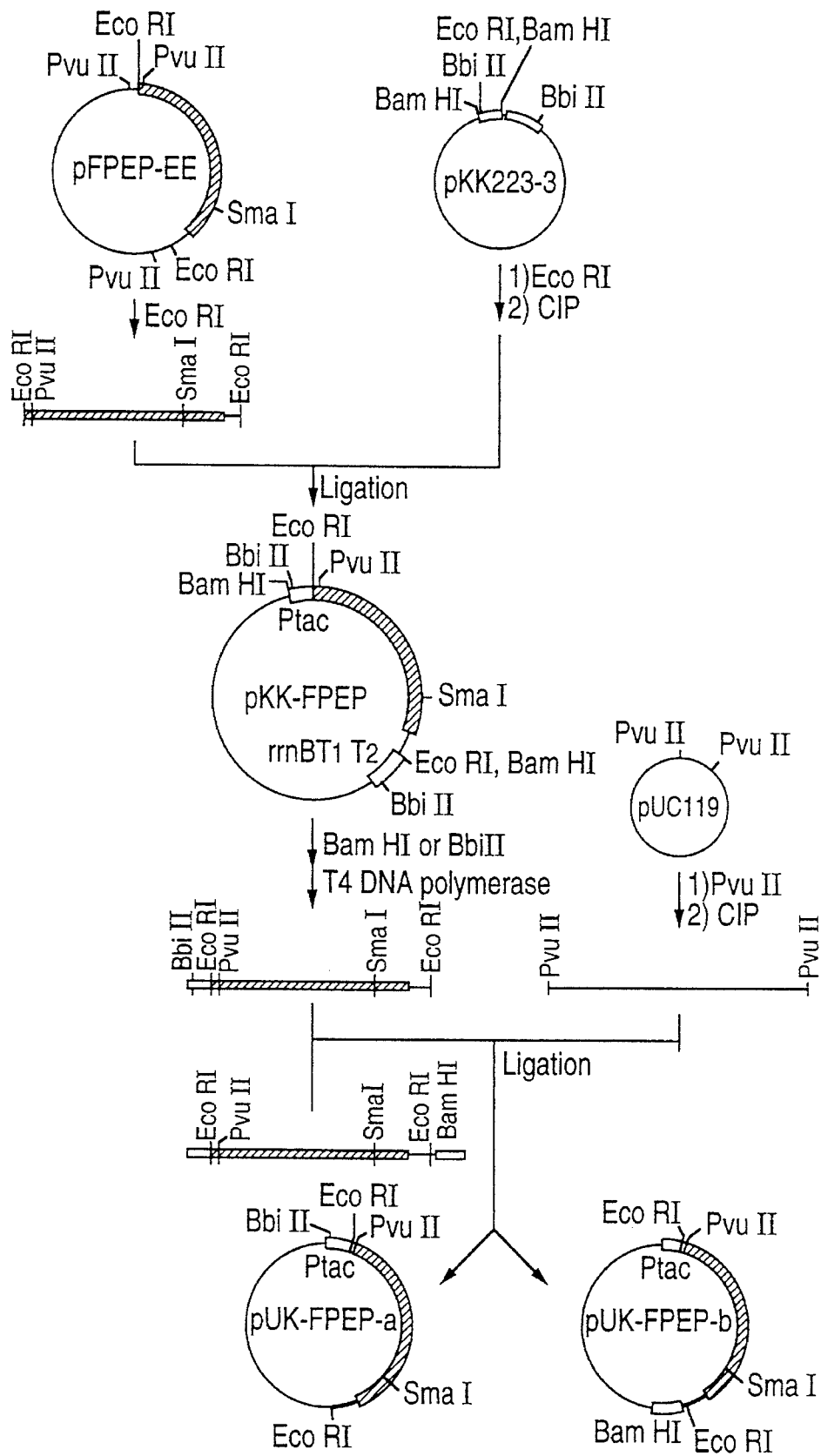
FIG. 4 represents pan of the process for construction of expression plasmids pUK-FPEP-a and pUK-FPEP-b starting from an intermediate plasmid pFPEPO4: Construction of pUK-FPEP-a and pUK-FPEP-b starting with pFPEP-EE.

In the next step of the vector construction, as shown in FIG. 4, the whole coding region, together with a short downstream non-coding region, is cleaved out from pFPEP-EE by EcoRI. The fragment is then inserted into the EcoRI site of the expression vector, pKK223-3, to provide pKK-FPEP in which the transcription of the prolylendopeptidase gene is under the control of the tac promoter.

The replication origin of pKK223-3 originates from pBR322 and the copy number of this expression vector in a single cell is usually low. Because of the higher dose effect of the gene a high copy number plasmid is preferable as an expression vector for a higher expression level. Therefore, a) a set of the promoter and the coding region or b) a set of the promoter, the coding region and the terminator is excised by BamHi or BbiII, respectively, and transplanted into the high copy number plasmid, pUC119. Since the peptidase gene is transferred from pKK-FPEP together with the tac promoter, the original lac promoter of pUC119 is removed by PvuII in order to avoid the double promoter. In between the blunt ends generated by this PvuII digestion either the gene set a) or the set b), which has been blunted by T4 DNA polymerase, is inserted to give pUK-FPEP-a or pUK-FPEP-b, respectively (FIG. 4).

For overexpression of prolylendopeptidase, *E. coli*, JM 109, is transformed by pUK-FPEP-a or pUK-FPEP-b. The transformants are selected on LB plates containing 50 µg/ml of ampicillin and grown in LB medium with the ampicillin overnight. For expression of prolylendopeptidase 100 ml of CIRCLEGROW (BIO 101, Inc., Vista, Calif.) medium (without ampicillin) is inoculated with 2 ml of the overnight culture and shaken at 37° C. In a preliminary experiment the maximum expression level in the transformant harboring pUK-FPEP-a (13,500 units/L) is found twice as high as that for pUK-FPEP-b (6,600 Units/L) when the expression is boosted with 1 mM IPTG on a half day after the inoculation. Without the IPTG the basal expression levels for both clones are still quite high; in the case of pUK-FPEP-b it is even higher (8,060 units/L) than the level obtained by the addition of IPTG.

Since pUK-FPEP-a shows the highest expression level, reaching 39 times of the enzyme activity obtained by *F. meningosepticum* and 4 times of the expression level attained with the pFPH5-KD50, the time course of the expression is followed with or without the addition of IPTG (Table IV). As the growth, monitored by the absorbance of the culture broth at 550 nm, slowed down around 4 h after the inoculation, the activity of the enzyme increases linearly along the time course. Without the boosting the expression by the IPTG the activity increases further linearly up to 20 h to attain the maximum level of 7,400 units/L at 24 h and then decreases. The specific activity of the endopeptidase stayed constant around 11 units/mg protein after 12 h. On the other hand, when 1 mM IPTG is added at 12 h, the increase is clearly enhanced immediately after the addition, reaching the highest expression level of 13,500 units/L at 28 h. A significant increase in the specific activity is also seen simultaneously with the sharp increase in the expression level and the maximum specific activity, 40 units/mg protein, is observed at 28 h and later, clearly demonstrating the effect of the IPTG induction on the tac promoter. Since a typical pure preparation of prolylendopeptidase from *F. meningosepticum* was reported to show a specific activity of 115 units/mg protein (Yoshimoto, T. et al., 1978 supra), the expressed enzyme accounts for over 30% of the total protein extracted from *E. coli*.

Such a high expression of prolylendopeptidase is also demonstrated in SDS-PAGE analysis. Already at 6 h after the inoculation, appearance of a new band is clearly noticed at the same position as the standard of prolylendopeptidase, and the expansion of that band demonstrates the increase in the expression level clearly during the time course from 12 h to 28 h, concomitantly with the change of the total activity of the enzyme.

solved in 20 mM phosphate buffer, pH 6.2 and dialyzed against the same buffer. The dialyzate is applied to a CM52 column (carboxymethyl-cellulose, Whatman BioSystems Ltd.) equilibrated with the same buffer. The enzyme is eluted by a linear gradient of NaCl. Active fractions are combined, concentrated by ultrafiltration with a Amicons cell and a YM30 MEMBRANE (Amicon Div., W.R.Grace & Co.) and dialyzed against 20 mM phosphate buffer, pH 6.8. Prolylendopeptidase is further purified on a MONO S HR 10/10 COLUMN (Pharmacia LKB Biotechnology AB). With a NaCl gradient (0–0.075M) the endopeptidase is eluted in a sharp peak around 0.035M of NaCl. The purified enzyme appears to be homogeneous yielding only a single band in SDS-PAGE.

EXAMPLE 8

Production of luteinizing hormone-releasing hormone (LH-RH)

Since LH-RH (a decapeptide) has a proline residue at the penultimate position, it is prepared from the nonapeptide precursor and glycine-amide. In the presence of a catalytic amount of prolylendopeptidase (0.08 µM), 1 mM of the precursor and 2.0M glycineamide are incubated in 60% glycerol at pH 7.0 and 30° C. In 48 h the coupling comes to equilibrium with the hydrolysis and LH-RH is obtained in the conversion of 67% in a quantitative yield (97% isolation yield). The rest of the precursor is recovered in HPLC purification and no side reaction is noticed.

TABLE IV

Expression of prolylendopeptidase in *E. coli* (JM109) harboring pUK-FPEP-a.[a]

| | Without IPTG | | | With IPTG[b] | | |
|---|---|---|---|---|---|---|
| Time (h) | Absorbance at 550 nm | Total activity (unit/L) | Specific activity (unit/mg protein) | Absorbance at 550 nm | Total activity (unit/L) | Specific activity (unit/mg protein) |
| 0 | 0.15 | 14.5 | 17.7 | 0.15 | 14.5 | 17.7 |
| 4 | 2.17 | 369 | 2.3 | 2.18 | 351 | 2.5 |
| 8 | 3.92 | 2206 | 7.1 | 3.90 | 1977 | 8.3 |
| 12 | 4.63 | 3601 | 11.1 | 4.71 | 2915 | 8.6 |
| 14 | 5.12 | 4119 | 10.7 | 4.87 | 4762 | 14.8 |
| 16 | 5.86 | 5038 | 11.3 | 5.06 | 7708 | 24.7 |
| 20 | 6.24 | 7129 | 13.6 | 4.88 | 11340 | 35.2 |
| 24 | 6.35 | 7416 | 12.7 | 4.79 | 12850 | 37.5 |
| 28 | 6.60 | 6120 | 11.0 | 5.13 | 13490 | 39.8 |
| 36 | 5.60 | 4683 | 10.9 | 4.86 | 10400 | 40.4 |

[a]The transformed *E. coli* is cultured in CIRCLEGROW medium at 37° C. with agitation in a rotary shaker (120 rpm). Growth of the cells is monitored by absorbance at 550 nm and specific activity and total activity are followed over 36h after inoculation.
[b]To boost the expression 1 mM IPTG is added at 12 h.

EXAMPLE 7

Production of recombinant prolylendopeptidase

Since prolylendopeptidase is expressed in *E. coli* in a soluble and active form and the expression level is so high (more than 30% of the total extracted protein), the isolation of the expressed enzyme is quite straightforward.

*E. coli* cells transformed with the expression plasmid pUK-FPEP-a are cultured in the CIRCL-EGROW medium with boosting by IPTG for 28 hours at 37 ° C. *E. coli* cells are harvested by centrifugation (3,000 g for 10 min) and washed with cold 0.1M HEPES buffer, pH 7.4. The washed cells are re-suspended in 0.1M HEPES and disrupted by sonication intermittently over 20 min with a SONIFIER 450 (BRANSON Sonic Power Co.). The lysate is then fractionated with ammonium sulfate precipitation. The protein precipitated at 65–90% saturated ammonium sulfate is dis-

EXAMPLE 9

Production of oxytocin

Oxytocin, a nonapeptide having a proline residue at the third position from its c-terminus, is obtained by coupling the precursor of the first seven residues to leucylglycineamide with prolylendopeptidase. In a typical example 1 mM of the oxytocin precursor [1–7] and 0.8M leucylglycineamide are incubated with 0.13 µM prolylendopeptidase in 60% glycerol at pH 6.5 and 30° C. The coupling proceeds to reach an equilibrium after 48 h and 55% of the precursor is convened to oxytocin in a quantitative yield (91% isolation yield). No by-product is detected and 43% of the starting material is recovered.

EXAMPLE 10

Alternative method for purification of recombinant prolylendopeptidase

E. coli cells expressing prolylendopeptidase are harvested by centrifugation (10,000 g for 10 min) and washed with cold 0.1M Tris-HCl buffer, pH 8.0. The washed cells are re-suspended in 0.5M sucrose solution containing 5 mM EDTA buffered at pH 8.0 with 0.1M Tris-HCl. Lysozyme (160 μg/ml) is added to the suspension and the mixture is left on ice for 2 min before dilution with the same volume of ice-cold water. The diluted cell suspension is further left on ice for 30 min and then centrifuged at 10,000 g for 20 min. The supernatant is diluted again with the same volume of ice-cold water and its pH is adjusted to 7.0 with 1 N NaOH. The obtained crude enzyme solution (a periplasma fraction) is directly applied to a CM 52 column (Whatman BioSystems Ltd.) equilibrated with 20 mM phosphate buffer, pH 6.8. The enzyme is eluted in a single peak with a linear gradient (0–0.25M) of NaCl. In this alternative purification method with the osmotic shock procedure, prolylendopeptidase is purified to homogeneity as judged by SDS-page analysis with a single chromatography step.

EXAMPLE 11

Properties of recombinant prolylendopepadase from *Flavobacterium meningosepticum* expressed in *E. coil*

The method (B) described in Example 5 is modified to assay purified prolylendopeptidase. DTT (1 mM) and BSA (100 μg/ml) are included in the buffer solution of 0.1M phosphate (pH 7.0) for the assay to improve reproducibility and accuracy of the kinetic measurement. To 0.94 ml of this buffer solution is added 0.05 ml of 4 mM Z-Gly-Pro-p-nitroanilide in 40% dioxane. After 3 min preincubafion at 30° C., 0.01 ml of the enzyme solution obtained in example 10 is added to the mixture and changes of the absorbance at 410 nm is followed at 30° C.

In a typical purification the enzyme with a specific activity higher than 120 units/mg protein is obtained. The molecular weight is estimated to be 71,000 and 74,000 by gel filtration with a TSK-GEL G3000SW column (Tosoh Corp.) and SDS-PAGE, respectively. The enzyme shows an extinction coefficient E(1%/280 nm) of 15.5. There are two cysteine residues according to the deduced amino acid sequence with SEQ ID No. 1, but no free sulfhydryl group is detectable by titration with p-chloromercuribenzoic acid under a denatured condition with 8M urea. The N-terminal sequence of the recombinant prolylendopeptidase is found to start with Ala and follows with Gln, Asn, Ser, Asn, X (unknown), Leu, Lys, Tyr, and Pro, proving that the first 19 amino acid residues shown in the sequence with SEQ ID No. 1 encode a signal sequence and are missing from the N-terminus of the matured enzyme.

Deposited Microorganisms

E. coli TG 1/pFPEPO3 was deposited under the Budapest Treaty with with the Fermentation Research Institute, Agency of Industrial Science and Technology (FRI), 1–3, Higashi 1-chome, Tsukuba-shi, Ibaraki, Japan, on Jul. 5, 1991, as FERM BP-3466.

We claim:

1. A purified recombinant DNA molecule comprising a DNA sequence encoding a prokaryotic prolylendopeptidase from *Flavobacterium spec.* having the amino acid sequence shown in SEQ ID No. 1.

2. The purified recombinant DNA molecule according to claim 1, comprising the DNA sequence shown in SEQ ID No. 1.

3. The purified recombinant DNA molecule according to claim 1, comprising the DNA sequence encoding the mature prolylendopeptidase coding region shown in SEQ ID. No. 1.

4. The purified recombinant DNA molecule according to claim 1, which is plasmid pFPEP03 (FERM BP-3466).

5. The purified recombinant DNA molecule according to claim 1, comprising the 2.6 kb HincII fragment of pFPEP03 (FERM BP-3466).

6. The purified recombinant DNA molecule according to claim 1, in which the 5' noncoding sequence of the prolylendopeptidase gene shown in SEQ ID No. 1 has 120 bp.

7. The recombinant DNA molecule according to claim 1, which is an expression vector comprising the DNA sequence encoding the prokaryotic prolylendopeptidase operably linked with an expression control sequence.

8. The recombinant DNA molecule according to claim 7, wherein the expression control sequence comprises *E. coli tac* promoter.

9. The recombinant DNA molecule according to claim 7, wherein the expression vector is selected from the group of vectors consisting of pUK-FPEP-a and pUK-FPEP-b.

10. The recombinant DNA molecule according to claim 7, in which the 5' noncoding sequence of the prolylendopeptidase gene shown in SEQ ID No. 1 has 120 bp.

11. The recombinant DNA molecule according to claim 10, which is pFPH5-KD50.

12. A method of using the recombinant DNA molecule according to claim 1, which comprises the step of culturing a host organism transformed with an expression vector comprising the recombinant DNA molecule according to claim 1 to produce the prokaryotic prolylendopeptidase having the amino acid sequence shown in SEQ ID NO. 1 encoded by the DNA molecule.

13. The method according to claim 12, which further comprises the step of recovering the prokaryotic prolylendopeptidase from the host organism.

14. The method according to claim 12, wherein the host organism is *E. coli*.

15. A host cell transformed with a recombinant DNA molecule comprising a DNA sequence encoding a prokaryotic prolylendopeptidase from *Flavobacterium spec.* having the amino acid sequence shown in SEQ ID No. 1.

16. The host cell according to claim 15, which is *E. coli* transformed with an expression vector comprising the DNA sequence encoding a prokaryotic prolylendopeptidase from *Flavobacterium spec.* having the amino acid sequence shown in SEQ ID No. 1 operably linked with an expression control sequence, and which is capable of producing the prokaryotic prolylendopeptidase encoded by the expression vector.

17. A purified signal sequence having the amino acid sequence of the signal sequence shown in SEQ ID No. 1.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 2636 base pairs
        ( B ) TYPE: nucleic acid
        ( C ) STRANDEDNESS: double
        ( D ) TOPOLOGY: linear ( i i ) MOLECULE TYPE: genomic DNA ( i i i ) HYPOTHETICAL:

( i v ) ANTI-SENSE:

( v ) FRAGMENT TYPE:

( v i ) ORIGINAL SOURCE:
        ( A ) ORGANISM: Flavobacterium meningosepticum
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE: plasmid pFPEP03
        ( A ) LIBRARY:
        ( B ) CLONE:

( v i i i ) POSITION IN GENOME:
        ( A ) CHROMOSOME/SEGMENT:
        ( B ) MAP POSITION:

( C ) UNITS:

( i x ) FEATURE:
    ( A ) NAME/KEY:
    ( B ) LOCATION: 1 to 259
    ( C ) IDENTIFICATION METHOD:
    ( D ) OTHER INFORMATION: /note="promoter region"

( i x ) FEATURE:
    ( A ) NAME/KEY:
    ( B ) LOCATION: 260 to 316
    ( C ) IDENTIFICATION METHOD:
    ( D ) OTHER INFORMATION: /note="signal sequence"

( i x ) FEATURE:
    ( A ) NAME/KEY:
    ( B ) LOCATION: 317 to 2374
    ( C ) IDENTIFICATION METHOD:
    ( D ) OTHER INFORMATION: /note="mature prolylendopeptidase coding region"

( i x ) FEATURE:
    ( A ) NAME/KEY:
    ( B ) LOCATION: 2375 to 2377
    ( C ) IDENTIFICATION METHOD:
    ( D ) OTHER INFORMATION: /note="stop codon"

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:1:

```
GTTGACGGTA  AAGTAGTATT  TACTAAAAAG  AGAGATAACA  GGTCTTACGT            50

ATCTGTAGCA  CCAGATGCTT  AATTAAAGCA  TTTTATAAAA  ATTAAAACCT           100

CAACGAAAGT  TGAGGTTTTT  TTTGTCTCAA  AAACCTAACA  GGTTTCTGAA           150

ACCTGTTAGG  TTTATTGTGT  ATAGGGGTTA  AGTGATACAT  ATTTATACTG           200

TGCTGAAATG  CGAATCTGAT  TATTCGAAAA  TTCTCCCTAT  TTTTGATAAA          250

ACCAATTCT  ATG  AAG  TAC  AAC  AAA  CTT  TCT  GTG  GCA  GTT  GCA  GCC      295
           Met  Lys  Tyr  Asn  Lys  Leu  Ser  Val  Ala  Val  Ala  Ala
           -19             -15                      -10

TTT  GCT  TTT  GCA  GCT  GTA  TCA  GCA  CAA  AAT  TCT  AAT  GTT  TTG       337
Phe  Ala  Phe  Ala  Ala  Val  Ser  Ala  Gln  Asn  Ser  Asn  Val  Leu
          -5                 -1   +1                      5

AAA  TAT  CCC  GAA  ACT  AAA  AAA  GTA  AGC  CAT  ACC  GAT  ACC  TAT       379
Lys  Tyr  Pro  Glu  Thr  Lys  Lys  Val  Ser  His  Thr  Asp  Thr  Tyr
               10                 15                      20

TTT  GGT  ACT  CAG  GTA  TCC  GAT  CCT  TAT  CGC  TGG  CTG  GAA  GAC       421
Phe  Gly  Thr  Gln  Val  Ser  Asp  Pro  Tyr  Arg  Trp  Leu  Glu  Asp
                25                      30                         35

GAC  AGA  GCC  GAA  GAT  ACA  AAA  GCC  TGG  GTA  CAA  CAG  GAA  GTT       463
Asp  Arg  Ala  Glu  Asp  Thr  Lys  Ala  Trp  Val  Gln  Gln  Glu  Val
                    40                      45

AAA  TTT  ACA  CAA  GAC  TAC  CTT  GCA  CAG  ATT  CCT  TTC  CGT  GAT       505
Lys  Phe  Thr  Gln  Asp  Tyr  Leu  Ala  Gln  Ile  Pro  Phe  Arg  Asp
50                       55                      60

CAG  CTT  AAA  AAG  CAA  TTA  ATG  GAC  ATC  TGG  AAT  TAT  GAG  AAA       547
Gln  Leu  Lys  Lys  Gln  Leu  Met  Asp  Ile  Trp  Asn  Tyr  Glu  Lys
          65                     70                         75
```

```
ATT TCA GCA CCG TTT AAA AAA GGT AAA TAC ACC TAT TTT TCT         589
Ile Ser Ala Pro Phe Lys Lys Gly Lys Tyr Thr Tyr Phe Ser
        80                      85                  90

AAA AAT GAT GGT CTT CAG GCG CAA TCT GTA CTT TAC AGA AAA         631
Lys Asn Asp Gly Leu Gln Ala Gln Ser Val Leu Tyr Arg Lys
            95                  100                 105

GAT GCG GCA GGT AAG ACG GAA GTA TTT TTA GAT CCT AAT AAG         673
Asp Ala Ala Gly Lys Thr Glu Val Phe Leu Asp Pro Asn Lys
                110                 115

TTT TCG GAA AAA GGA ACC ACT TCT CTG GCA AGT GTT TCT TTT         715
Phe Ser Glu Lys Gly Thr Thr Ser Leu Ala Ser Val Ser Phe
120                 125                 130

AAT AAA AAA GGA ACT CTG GTC GCT TAT AGT ATA TCA GAA GGA     757
    Asn Lys Lys Gly Thr Leu Val Ala Tyr Ser Ile Ser Glu Gly
        135                 140                 145

GGT TCG GAC TGG AAT AAG ATT ATT ATT CTG GAT GCG GAA ACC         799
Gly Ser Asp Trp Asn Lys Ile Ile Ile Leu Asp Ala Glu Thr
            150                 155                 160

AAA AAG CAA CTT GAT GAA ACT CTA TTG GAT GTT AAG TTC AGT         841
Lys Lys Gln Leu Asp Glu Thr Leu Leu Asp Val Lys Phe Ser
                165                 170                 175

GGA ATT TCA TGG TTG GGA GAT GAA GGA TTC TTT TAT TCC AGC         883
Gly Ile Ser Trp Leu Gly Asp Glu Gly Phe Phe Tyr Ser Ser
                    180                 185

TAT GAT AAG CCA AAA GAA GGA AGC GTA CTT TCC GGG ATG ACA         925
Tyr Asp Lys Pro Lys Glu Gly Ser Val Leu Ser Gly Met Thr
190                 195                 200

GAT AAA CAC AAA GTT TAT TTT CAT AAG TTA GGA ACG AAG CAG         967
Asp Lys His Lys Val Tyr Phe His Lys Leu Gly Thr Lys Gln
    205                 210                 215

TCT CAG GAT GAA TTG ATT ATT GGG GGT GAT AAA TTT CCA AGA         1009
Ser Gln Asp Glu Leu Ile Ile Gly Gly Asp Lys Phe Pro Arg
        220                 225                 230

AGA TAT ATA GGA GCT TAT GTA ACC GAT GAT CAG AGA TAT CTG         1051
Arg Tyr Ile Gly Ala Tyr Val Thr Asp Asp Gln Arg Tyr Leu
            235                 240                 245

GTG GTT TCG GCT GCA AAT GCA ACC AAC GGA AAC GAG CTT TAC         1093
Val Val Ser Ala Ala Asn Ala Thr Asn Gly Asn Glu Leu Tyr
                250                 255

ATT AAA GAC CTG AAG AAT AAA ACA GAT TTT ATT CCG ATT ATT         1135
Ile Lys Asp Leu Lys Asn Lys Thr Asp Phe Ile Pro Ile Ile
260                 265                 270

ACA GGT TTT GAT AGC AAT GTA AAT GTT GCA GAT ACC GAC GGT         1177
Thr Gly Phe Asp Ser Asn Val Asn Val Ala Asp Thr Asp Gly
    275                 280                 285

GAT ACG CTT TAT TTG TTC ACC GAT AAA GAT GCA CCG AAT AAG     1219
    Asp Thr Leu Tyr Leu Phe Thr Asp Lys Asp Ala Pro Asn Lys
        290                 295                 300

CGA CTG GTA AAA ACA ACG ATT CAG AAT CCA AAA GCG GAA ACA         1261
Arg Leu Val Lys Thr Thr Ile Gln Asn Pro Lys Ala Glu Thr
            305                 310                 315

TGG AAA GAT GTG ATT GCT GAA ACC ACC GAA CCA TTC CAA ATC         1303
Trp Lys Asp Val Ile Ala Glu Thr Thr Glu Pro Phe Gln Ile
                320                 325

AAT ACG GGA GGC GGT TAT TTC TTT GCT ACT TAT ATG AAA GAT         1345
Asn Thr Gly Gly Gly Tyr Phe Phe Ala Thr Tyr Met Lys Asp
330                 335                 340

GCA ATC GAT CAG GTA AAG CAA TAT GAT AAA AAC GGA AAG CTT         1387
Ala Ile Asp Gln Val Lys Gln Tyr Asp Lys Asn Gly Lys Leu
    345                 350                 355
```

| | | | | | | | | | | | | | |
|---|---|---|---|---|---|---|---|---|---|---|---|---|---|
| GTA | AGG | GCT | ATA | AAA | TTA | CCG | GGA | AGT | GGT | AAT | GCA | AGC | GGT | 1429 |
| Val | Arg | Ala | Ile | Lys | Leu | Pro | Gly | Ser | Gly | Asn | Ala | Ser | Gly | |
| | | 360 | | | | 365 | | | | | 370 | | | |
| TTT | GGG | GGT | GAA | AAA | ACG | GAA | AAG | GAT | CTG | TAT | TAC | TCT | TTC | 1471 |
| Phe | Gly | Gly | Glu | Lys | Thr | Glu | Lys | Asp | Leu | Tyr | Tyr | Ser | Phe | |
| | | | | 375 | | | | 380 | | | | | 385 | |
| ACC | AAT | TAT | ATT | ACG | CCG | CCA | ACG | ATC | TTT | AAA | TAT | AAT | GTA | 1513 |
| Thr | Asn | Tyr | Ile | Thr | Pro | Pro | Thr | Ile | Phe | Lys | Tyr | Asn | Val | |
| | | | | 390 | | | | | 395 | | | | | |
| ACA | ACA | GGT | AAT | TCT | GAA | GTT | TAC | CAG | AAG | CCG | AAA | GTG | AAG | 1555 |
| Thr | Thr | Gly | Asn | Ser | Glu | Val | Tyr | Gln | Lys | Pro | Lys | Val | Lys | |
| 400 | | | | | 405 | | | | | 410 | | | | |
| TTC | AAT | CCG | GAA | AAT | TAT | GTT | TCG | GAG | CAG | GTA | TTC | TAT | ACT | 1597 |
| Phe | Asn | Pro | Glu | Asn | Tyr | Val | Ser | Glu | Gln | Val | Phe | Tyr | Thr | |
| | 415 | | | | | 420 | | | | | 425 | | | |
| TCA | TCT | GAC | GGG | ACT | AAG | ATT | CCG | ATG | ATG | ATC | AGC | TAC | AAG | 1639 |
| Ser | Ser | Asp | Gly | Thr | Lys | Ile | Pro | Met | Met | Ile | Ser | Tyr | Lys | |
| | | 430 | | | | | 435 | | | | | 440 | | |
| AAA | GGC | CTG | AAA | AAA | GAC | GGT | AAA | AAC | CCT | ACA | ATA | TTA | TAC | 1681 |
| Lys | Gly | Leu | Lys | Lys | Asp | Gly | Lys | Asn | Pro | Thr | Ile | Leu | Tyr | |
| | | | 445 | | | | 450 | | | | | 455 | | |
| AGC | TAC | GGA | GGA | TTT | AAT | ATC | AGT | CTT | CAG | CCT | GCT | TTC | TCT | 1723 |
| Ser | Tyr | Gly | Gly | Phe | Asn | Ile | Ser | Leu | Gln | Pro | Ala | Phe | Ser | |
| | | | 460 | | | | | 465 | | | | | | |
| GTT | GTA | AAT | GCA | ATC | TGG | ATG | GAA | AAC | GGT | GGT | ATT | TAT | GCT | 1765 |
| Val | Val | Asn | Ala | Ile | Trp | Met | Glu | Asn | Gly | Gly | Ile | Tyr | Ala | |
| 470 | | | | | 475 | | | | | 480 | | | | |
| GTT | CCG | AAT | ATC | CGT | GGT | GGT | GGA | GAA | TAT | GGT | AAG | AAA | TGG | 1807 |
| Val | Pro | Asn | Ile | Arg | Gly | Gly | Gly | Glu | Tyr | Gly | Lys | Lys | Trp | |
| | 485 | | | | | 490 | | | | | 495 | | | |
| CAT | GAT | GCC | GGA | ACT | AAA | ATG | CAG | AAA | AAG | AAT | GTA | TTT | AAT | 1849 |
| His | Asp | Ala | Gly | Thr | Lys | Met | Gln | Lys | Lys | Asn | Val | Phe | Asn | |
| | | 500 | | | | 505 | | | | | 510 | | | |
| GAC | TTT | ATT | GCA | GCC | GGA | GAG | TAC | TTA | CAG | AAA | AAC | GGT | TAT | 1891 |
| Asp | Phe | Ile | Ala | Ala | Gly | Glu | Tyr | Leu | Gln | Lys | Asn | Gly | Tyr | |
| | | | 515 | | | | | 520 | | | | | 525 | |
| ACA | TCT | AAG | GAA | TAT | ATG | GCG | CTT | TCC | GGA | CGT | TCC | AAC | GGC | 1933 |
| Thr | Ser | Lys | Glu | Tyr | Met | Ala | Leu | Ser | Gly | Arg | Ser | Asn | Gly | |
| | | | | 530 | | | | | 535 | | | | | |
| GGT | CTT | CTT | GTA | GGG | GCT | ACG | ATG | ACA | ATG | CGC | CCT | GAT | TTG | 1975 |
| Gly | Leu | Leu | Val | Gly | Ala | Thr | Met | Thr | Met | Arg | Pro | Asp | Leu | |
| 540 | | | | | 545 | | | | | 550 | | | | |
| GCA | AAA | GTT | GCA | TTC | CCG | GGA | GTA | GGA | GTA | CTG | GAT | ATG | CTT | 2017 |
| Ala | Lys | Val | Ala | Phe | Pro | Gly | Val | Gly | Val | Leu | Asp | Met | Leu | |
| 555 | | | | | 560 | | | | | 565 | | | | |
| CGT | TAT | AAT | AAG | TTT | ACA | GCT | GGT | GCC | GGT | TGG | GCT | TAT | GAT | 2059 |
| Arg | Tyr | Asn | Lys | Phe | Thr | Ala | Gly | Ala | Gly | Trp | Ala | Tyr | Asp | |
| | | 570 | | | | 575 | | | | | 580 | | | |
| TAC | GGT | ACA | GCA | GAA | GAC | AGC | AAG | GAA | ATG | TTT | GAA | TAC | CTG | 2101 |
| Tyr | Gly | Thr | Ala | Glu | Asp | Ser | Lys | Glu | Met | Phe | Glu | Tyr | Leu | |
| | | | 585 | | | | 590 | | | | | 595 | | |
| AAG | TCT | TAT | TCT | CCG | GTA | CAT | AAC | GTA | AAA | GCC | GGA | ACT | TGT | 2143 |
| Lys | Ser | Tyr | Ser | Pro | Val | His | Asn | Val | Lys | Ala | Gly | Thr | Cys | |
| | | | | 600 | | | | 605 | | | | | | |
| TAT | CCT | TCT | ACG | ATG | GTC | ATT | ACA | AGT | GAT | CAT | GAT | GAC | AGA | 2185 |
| Tyr | Pro | Ser | Thr | Met | Val | Ile | Thr | Ser | Asp | His | Asp | Asp | Arg | |
| 610 | | | | | 615 | | | | | 620 | | | | |
| GTT | GTT | CCC | GCT | CAT | TCA | TTT | AAG | TTC | GGT | TCA | GAA | TTA | CAG | 2227 |
| Val | Val | Pro | Ala | His | Ser | Phe | Lys | Phe | Gly | Ser | Glu | Leu | Gln | |
| 625 | | | | | 630 | | | | | 635 | | | | |

-continued

| | | | | | | | | | | | | | | |
|---|---|---|---|---|---|---|---|---|---|---|---|---|---|---|
| GCA | AAA | CAA | TCT | TGT | AAG | AAT | CCT | ATT | CTT | ATC | CGT | ATT | GAA | 2269 |
| Ala | Lys | Gln | Ser | Cys | Lys | Asn | Pro | Ile | Leu | Ile | Arg | Ile | Glu | |
| | | 640 | | | | | 645 | | | | | 650 | | |
| ACA | AAT | GCT | GGA | CAC | GGA | GCA | GGA | CGT | TCC | ACA | GAA | CAG | GTC | 2311 |
| Thr | Asn | Ala | Gly | His | Gly | Ala | Gly | Arg | Ser | Thr | Glu | Gln | Val | |
| | | | 655 | | | | | 660 | | | | | 665 | |
| GTT | GCT | GAG | AAT | GCC | GAT | CTG | CTT | TCA | TTC | GCA | TTA | TAT | GAA | 2353 |
| Val | Ala | Glu | Asn | Ala | Asp | Leu | Leu | Ser | Phe | Ala | Leu | Tyr | Glu | |
| | | | | 670 | | | | | 675 | | | | | |
| ATG | GGA | ATT | AAA | AGT | TTA | AAA | TAG | ATTTCAAATA | CTAAATATAA | | | | | 2397 |
| Met | Gly | Ile | Lys | Ser | Leu | Lys | | | | | | | | |
| 680 | | | | | 685 | | | | | | | | | |

| | | | | | |
|---|---|---|---|---|---|
| AACAGGCAGG | TCTTTTTGAT | TTGCCTGTTT | TTTTATGATA | CTATTGAGTT | 2447 |
| TGGATTATGT | TAAATAGATT | AGATCATGAG | ATTTATATCT | CAGGAAATGA | 2497 |
| TTAACTTTAA | TACAAAATCT | TATACAATGG | AAAATCATGA | CATGACAACT | 2547 |
| TTAGTACAGG | TAATGAATAC | TTTGAAAAGA | AGAGGCGTGG | ACAAAGAAAT | 2597 |
| CCAGATGACA | GATGATAGGA | AATTTATACT | TCAGAATTC | | 2636 |

( 2 ) INFORMATION FOR SEQ ID NO:2:

( i ) SEQUENCE CHARACTERISTICS:
        ( A ) LENGTH: 44 base pairs
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:

(J) PUBLICATION DATE:
(K) RELEVANT RESIDUES IN SEQ ID NO:

(xi) SEQUENCE DESCRIPTION: SEQ ID NO:2:

GGGAGTAGGA GTTCTGGATA TGCTTCGTTA TAATAAGTTT ACTG    44

(2) INFORMATION FOR SEQ ID NO:3:

(i) SEQUENCE CHARACTERISTICS:
      (A) LENGTH: 54 base pairs
      (B) TYPE: nucleic acid
      (C) STRANDEDNESS: double
      (D) TOPOLOGY: linear (ii) MOLECULE TYPE: other nucleic acid (iii) HYPOTHETICAL:

(iv) ANTI-SENSE:

(v) FRAGMENT TYPE:

(vi) ORIGINAL SOURCE:
      (A) ORGANISM:
      (B) STRAIN:
      (C) INDIVIDUAL ISOLATE:
      (D) DEVELOPMENTAL STAGE:
      (E) HAPLOTYPE:
      (F) TISSUE TYPE:
      (G) CELL TYPE:
      (H) CELL LINE:
      (I) ORGANELLE:

(vii) IMMEDIATE SOURCE:
      (A) LIBRARY:
      (B) CLONE:

(viii) POSITION IN GENOME:
      (A) CHROMOSOME/SEGMENT:
      (B) MAP POSITION:
      (C) UNITS:

(ix) FEATURE:
      (A) NAME/KEY:
      (B) LOCATION:
      (C) IDENTIFICATION METHOD:
      (D) OTHER INFORMATION:

(x) PUBLICATION INFORMATION:
      (A) AUTHORS:
      (B) TITLE:
      (C) JOURNAL:
      (D) VOLUME:
      (E) ISSUE:
      (F) PAGES:
      (G) DATE:
      (H) DOCUMENT NUMBER:
      (I) FILING DATE:
      (J) PUBLICATION DATE:
      (K) RELEVANT RESIDUES IN SEQ ID NO:

(xi) SEQUENCE DESCRIPTION: SEQ ID NO:3:

AATTCATGAA GTACAACAAA CTTTCTGTGG CAGTTGCAGC CTTTGCTTTT    50

GCAG    54

(2) INFORMATION FOR SEQ ID NO:4:

(i) SEQUENCE CHARACTERISTICS:
      (A) LENGTH: 23 bases
      (B) TYPE: nucleic acid
      (C) STRANDEDNESS: single
      (D) TOPOLOGY: linear (ii) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:4:

AATTCATGAA GTACAACAAA CTT          23

( 2 ) INFORMATION FOR SEQ ID NO:5:

( i ) SEQUENCE CHARACTERISTICS:
    ( A ) LENGTH: 31 bases
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:5:

TCTGTGGCAG TTGCAGCCTT TGCTTTTGCA G                                                                    31

( 2 ) INFORMATION FOR SEQ ID NO:6:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:

( H ) DOCUMENT NUMBER:
                ( I ) FILING DATE:
                ( J ) PUBLICATION DATE:
                ( K ) RELEVANT RESIDUES IN SEQ ID NO:

( x i ) SEQUENCE DESCRIPTION: SEQ ID NO:6:

CACAGAAAGT TTGTTGTACT TCATG 25

( 2 ) INFORMATION FOR SEQ ID NO:7:

( i ) SEQUENCE CHARACTERISTICS:
                ( A ) LENGTH: 25 bases
                ( B ) TYPE: nucleic acid
                ( C ) STRANDEDNESS: single
                ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
                ( A ) ORGANISM:
                ( B ) STRAIN:
                ( C ) INDIVIDUAL ISOLATE:
                ( D ) DEVELOPMENTAL STAGE:
                ( E ) HAPLOTYPE:
                ( F ) TISSUE TYPE:
                ( G ) CELL TYPE:
                ( H ) CELL LINE:
                ( I ) ORGANELLE:

( v i i ) IMMEDIATE SOURCE:
                ( A ) LIBRARY:
                ( B ) CLONE:

( v i i i ) POSITION IN GENOME:
                ( A ) CHROMOSOME/SEGMENT:
                ( B ) MAP POSITION:
                ( C ) UNITS:

( i x ) FEATURE:
                ( A ) NAME/KEY:
                ( B ) LOCATION:
                ( C ) IDENTIFICATION METHOD:
                ( D ) OTHER INFORMATION:

( x ) PUBLICATION INFORMATION:
                ( A ) AUTHORS:
                ( B ) TITLE:
                ( C ) JOURNAL:
                ( D ) VOLUME:
                ( E ) ISSUE:
                ( F ) PAGES:
                ( G ) DATE:
                ( H ) DOCUMENT NUMBER:
                ( I ) FILING DATE:
                ( J ) PUBLICATION DATE:
                ( K ) RELEVANT RESIDUES IN SEQ ID NO:

( x i ) SEQUENCE DESCRIPTION: SEQ ID NO:7:

CTGCAAAAGC AAAGGCTGCA ACTGC 25